US009388408B2

(12) United States Patent
van Rooij et al.

(10) Patent No.: US 9,388,408 B2
(45) Date of Patent: *Jul. 12, 2016

(54) OLIGONUCLEOTIDE-BASED INHIBITORS COMPRISING LOCKED NUCLEIC ACID MOTIF

(71) Applicant: MiRagen Therapeutics, Inc., Boulder, CO (US)

(72) Inventors: Eva van Rooij, Utrecht (NL); Christina M. Dalby, Boulder, CO (US); Rusty L. Montgomery, Boulder, CO (US)

(73) Assignee: miRagen Therapeutics, Inc., Boulder, CO (US)

( * ) Notice: Subject to any disclaimer, the term of this patent is extended or adjusted under 35 U.S.C. 154(b) by 42 days.

This patent is subject to a terminal disclaimer.

(21) Appl. No.: 13/924,340

(22) Filed: Jun. 21, 2013

(65) Prior Publication Data
US 2013/0344135 A1 Dec. 26, 2013

Related U.S. Application Data

(60) Provisional application No. 61/662,746, filed on Jun. 21, 2012, provisional application No. 61/801,533, filed on Mar. 15, 2013.

(51) Int. Cl.
C12N 15/113 (2010.01)
C07H 21/04 (2006.01)

(52) U.S. Cl.
CPC ........ *C12N 15/113* (2013.01); *C12N 2310/113* (2013.01); *C12N 2310/315* (2013.01); *C12N 2310/3231* (2013.01); *C12N 2310/344* (2013.01); *C12N 2310/346* (2013.01)

(58) Field of Classification Search
None
See application file for complete search history.

(56) References Cited

U.S. PATENT DOCUMENTS

| | | | |
|---|---|---|---|
| 7,232,806 B2 | 6/2007 | Tuschl et al. | |
| 7,687,617 B2 | 3/2010 | Thrue et al. | |
| 8,222,221 B2 | 7/2012 | Corey et al. | |
| 8,304,397 B2 | 11/2012 | Olson et al. | |
| 8,481,507 B2 | 7/2013 | Olson et al. | |
| 8,642,751 B2 | 2/2014 | Dalby et al. | |
| 2005/0059005 A1 | 3/2005 | Tuschl et al. | |
| 2006/0185027 A1 | 8/2006 | Bartel et al. | |
| 2007/0287179 A1 | 12/2007 | Tuschl et al. | |
| 2007/0292878 A1 | 12/2007 | Raymond | |
| 2008/0050744 A1 | 2/2008 | Brown et al. | |
| 2008/0176766 A1 | 7/2008 | Brown et al. | |
| 2008/0214437 A1 | 9/2008 | Mohapatra et al. | |
| 2009/0105174 A1 | 4/2009 | Jayasena | |
| 2009/0137504 A1 | 5/2009 | Echwald et al. | |
| 2009/0143326 A1 | 6/2009 | Obad et al. | |
| 2009/0180957 A1 | 7/2009 | Olson et al. | |
| 2009/0286969 A1 | 11/2009 | Esau et al. | |
| 2009/0291906 A1 | 11/2009 | Esau et al. |
| 2009/0291907 A1 | 11/2009 | Esau et al. |
| 2009/0293148 A1 | 11/2009 | Ren et al. |
| 2009/0326049 A1 | 12/2009 | Aristarkhov et al. |
| 2010/0004320 A1 | 1/2010 | Elmen et al. |
| 2010/0029003 A1 | 2/2010 | Bartel et al. |
| 2010/0173288 A1 | 7/2010 | Zhang et al. |
| 2010/0210712 A1 | 8/2010 | Hansen et al. |
| 2010/0269183 A1 | 10/2010 | Olson et al. |
| 2010/0280094 A1 | 11/2010 | Beuvink et al. |
| 2010/0292297 A1 | 11/2010 | Wang et al. |
| 2010/0298410 A1 | 11/2010 | Obad et al. |
| 2011/0071211 A1 | 3/2011 | Thum et al. |
| 2011/0098338 A1 | 4/2011 | Hajjar et al. |
| 2011/0105593 A1 | 5/2011 | Steel et al. |
| 2011/0117560 A1 | 5/2011 | Spinale et al. |
| 2011/0152352 A1 | 6/2011 | Hata et al. |
| 2011/0160285 A1 | 6/2011 | Anderson et al. |
| 2011/0224277 A1 | 9/2011 | Esau et al. |
| 2011/0294869 A1 | 12/2011 | Petersen |
| 2011/0313019 A1 | 12/2011 | Swayze et al. |
| 2012/0035243 A1 | 2/2012 | Olson et al. |
| 2012/0041052 A1 | 2/2012 | Beuvink et al. |
| 2012/0083596 A1 | 4/2012 | Elmén et al. |

(Continued)

FOREIGN PATENT DOCUMENTS

| | | |
|---|---|---|
| CN | 101386848 | 3/2009 |
| EP | 1959012 | 8/2008 |
| EP | 2113567 | 11/2009 |
| EP | 2194129 | 6/2010 |
| EP | 2208798 | 7/2010 |

(Continued)

OTHER PUBLICATIONS

Office Action for U.S. Appl. No. 13/327,507, mailed Feb. 27, 2013, 24 pages.

(Continued)

*Primary Examiner* — Jennifer McDonald
(74) *Attorney, Agent, or Firm* — Cooley LLP

(57) ABSTRACT

The present invention relates to chemical modification motifs for oligonucleotides. The oligonucleotides of the present invention, such as chemically modified antisense oligonucleotides, can have increased in vivo efficacy. The chemically modified oligonucleotides provide advantages in one or more of potency, efficiency of delivery, target specificity, toxicity, and/or stability. The chemically modified oligonucleotides have a specific chemical modification motif or pattern of locked nucleic acids (LNAs). The oligonucleotide (e.g. antisense oligonucleotide) can target RNA, such as miRNA or mRNA. Also provided herein are compositions comprising the chemically modified oligonucleotides and methods of using the chemically modified oligonucleotides as therapeutics for various disorders, including cardiovascular disorders.

14 Claims, 18 Drawing Sheets

(56) References Cited

U.S. PATENT DOCUMENTS

| | | |
|---|---|---|
| 2012/0114744 A1 | 5/2012 | Beuvink et al. |
| 2012/0172416 A1 | 7/2012 | Velin et al. |
| 2012/0322851 A1 | 12/2012 | Hardee et al. |
| 2013/0078225 A1 | 3/2013 | Zeng et al. |
| 2013/0079505 A1 | 3/2013 | Moeller et al. |
| 2013/0096290 A1 | 4/2013 | Brown |
| 2013/0109738 A1 | 5/2013 | Chang et al. |
| 2013/0137753 A1 | 5/2013 | Samant et al. |
| 2013/0150256 A1 | 6/2013 | Synnergren et al. |
| 2013/0156845 A1 | 6/2013 | Manoharan et al. |
| 2013/0157883 A1 | 6/2013 | Keller et al. |
| 2013/0171242 A1 | 7/2013 | Lim et al. |

FOREIGN PATENT DOCUMENTS

| | | |
|---|---|---|
| EP | 2388327 | 11/2011 |
| EP | 2388328 | 11/2011 |
| EP | 2447274 | 5/2012 |
| EP | 2205737 | 2/2013 |
| EP | 2559442 | 2/2013 |
| EP | 2604690 | 6/2013 |
| EP | 2610342 | 7/2013 |
| WO | WO 01/25478 | 4/2001 |
| WO | WO 2005/013901 | 2/2005 |
| WO | WO 2005/017145 | 2/2005 |
| WO | WO 2005/078096 | 8/2005 |
| WO | WO 2005/078139 | 8/2005 |
| WO | WO 2005/079397 | 9/2005 |
| WO | WO 2005/118806 | 12/2005 |
| WO | WO 2006/063356 | 6/2006 |
| WO | WO 2006/111512 | 10/2006 |
| WO | WO 2006/137941 | 12/2006 |
| WO | WO 2007/000668 | 1/2007 |
| WO | WO 2007/070483 | 6/2007 |
| WO | WO 2007/090073 | 8/2007 |
| WO | WO 2007/112754 | 10/2007 |
| WO | WO 2008/016924 | 2/2008 |
| WO | WO 2008/042231 | 4/2008 |
| WO | WO 2008/043521 | 4/2008 |
| WO | WO 2008/061537 | 5/2008 |
| WO | WO 2008/074328 | 6/2008 |
| WO | WO 2008/076324 | 6/2008 |
| WO | WO 2008/147839 | 12/2008 |
| WO | WO 2009/026576 | 2/2009 |
| WO | WO 2009/043353 | 4/2009 |
| WO | WO 2009/058818 | 5/2009 |
| WO | WO 2009/062169 | 5/2009 |
| WO | WO 2009/114681 | 9/2009 |
| WO | WO 2009/149182 | 12/2009 |
| WO | WO 2010/000665 | 1/2010 |
| WO | WO 2010/048585 | 4/2010 |
| WO | WO 2010/091204 | 8/2010 |
| WO | WO 2010/144485 | 12/2010 |
| WO | WO 2011/139911 | 11/2011 |
| WO | WO 2011/154553 | 12/2011 |
| WO | WO 2011/158191 | 12/2011 |
| WO | WO 2012/006577 | 1/2012 |
| WO | WO 2012/020307 | 2/2012 |
| WO | WO 2012/027206 | 3/2012 |
| WO | WO 2012/037254 | 3/2012 |
| WO | WO 2012/061810 | 5/2012 |
| WO | WO 2012/083005 | 6/2012 |
| WO | WO 2012/149646 | 11/2012 |
| WO | WO 2013/052965 | 4/2013 |
| WO | WO 2013/054113 | 4/2013 |
| WO | WO 2013/057527 | 4/2013 |
| WO | WO 2013/059496 | 4/2013 |
| WO | WO 2013/087907 | 6/2013 |
| WO | WO 2013/088338 | 6/2013 |
| WO | WO 2013/090457 | 6/2013 |
| WO | WO 2013/192576 | 12/2013 |

OTHER PUBLICATIONS

International Preliminary Report on Patentability for International Application No. PCT/US2011/065121, dated Jun. 18, 2013, 9 pages.

International Search Report and Written Opinion for International Application No. PCT/US2011/065121, mailed Jun. 5, 2012, 13 pages.

Office Action for U.S. Appl. No. 14/107,784, mailed Oct. 23, 2014, 26 pages.

International Search Report and Written Opinion for International Application No. PCT/US2013/047157, mailed Feb. 10, 2014, 12 pages.

Montgomery, R. L. et al., "Therapeutic inhibition of miR-208a improves cardiac function and survival during heart failure + supplemental material," Circulation, 124(14):1537-1547 (2011).

FIGURE 1A

| Molecule # | Sequence | Length | LNA/DNA |
|---|---|---|---|
| M-10101 | CtttTTgCtCGtCtTA | 16 | 9/7 |
| M-10679 | CtTtTTgCtCgTcTTa | 16 | 9/7 |
| M-10680 | CtTTTTgCtCgtCttA | 16 | 9/7 |
| M-10681 | CtTTtTgCTCgtCtTa | 16 | 9/7 |
| M-10682 | CtTtTtGcTcGtCtTA | 16 | 9/7 |
| M-10683 | CttTTtGcTCgTcTtA | 16 | 9/7 |
| M-10673 | CtTTTTgCtCgtCtTa | 16 | 9/7 |
| M-11184 | CtTTttGCtCgTcTtA | 16 | 9/7 |
| M-11293 | CtttTTgcTCGtCtTA | 16 | 9/7 |
| M-11294 | CTtttTgCtCGtCtTA | 16 | 9/7 |
| M-11295 | CTtttTGctCGTcTtA | 16 | 9/7 |
| M-11296 | CtttTTgCtCGtCTtA | 16 | 9/7 |
| M-11297 | CTttTtgCTCgTcTtA | 16 | 9/7 |
| M-11298 | CtTtTtGCtCgTcTtA | 16 | 9/7 |
| M-11299 | CttTTtGCtCgTcTtA | 16 | 9/7 |
| M-11300 | CTttTtGcTCgTcTtA | 16 | 9/7 |

A

| Molecule # | Alias | Sequence | Length | LNA/DNA |
|---|---|---|---|---|
| M-10707 | 208b_10101 | CcttTTgTtCGtCtTA | 16 | 9/7 |
| M-11283 | 208b_10679 | CcTtTTgTtCgTcTTa | 16 | 9/7 |
| M-11284 | 208b_10680 | CcTTTTgTtCgtCttA | 16 | 9/7 |
| M-11285 | 208b_10681 | CcTTtTgTTCgtCtTa | 16 | 9/7 |
| M-11286 | 208b_10682 | CcTtTtGtTcGtCtTA | 16 | 9/7 |
| M-11287 | 208b_10683 | CctTTtGtTCgTcTtA | 16 | 9/7 |
| M-11288 | 208b_10673 | CcTTTTgTtCgtCtTa | 16 | 9/7 |
| M-11289 | 208b_10626 | CcTTttGTtCgTcTtA | 16 | 9/7 |
| M-11290 | 208b_LNA_opt6 | CCttTtGTtCgTcTtA | 16 | 9/7 |

A

| Molecule # | Alias | Sequence | Length | LNA/DNA |
|---|---|---|---|---|
| M-11192 | 378_10101 | CtgaCTcCaAGtCcAG | 16 | 9/7 |
| M-11193 | 378_10680 | CtGACTcCaAgtCcaG | 16 | 9/7 |
| M-11194 | 378_10681 | CtGAcTcCAAgtCcAg | 16 | 9/7 |
| M-11195 | 378_10682 | CtGaCtCcAaGtCcAG | 16 | 9/7 |
| M-11196 | 378_10683 | CtgACtCcAAgTcCaG | 16 | 9/7 |
| M-11197 | 378_10673 | CtGACTcCaAgtCcAg | 16 | 9/7 |
| M-11198 | 378_10626 | CtGActCCaAgTcCaG | 16 | 9/7 |

| Molecule # | Alias | Sequence | Length | LNA/DNA |
|---|---|---|---|---|
| M-11185 | 29b_10101 | GattTCaAaTGgTgCT | 16 | 9/7 |
| M-11186 | 29b_10680 | GaTTTCaAaTggTgcT | 16 | 9/7 |
| M-11187 | 29b_10681 | GaTTtCaAATggTgCt | 16 | 9/7 |
| M-11188 | 29b_10682 | GaTtTcAaAtGgTgCT | 16 | 9/7 |
| M-11189 | 29b_10683 | GatTTcAaATgGtGcT | 16 | 9/7 |
| M-11190 | 29b_10673 | GaTTTCaAaTggTgCt | 16 | 9/7 |
| M-11191 | 29b_10626 | GaTTtcAAaTgGtGcT | 16 | 9/7 |

FIGURE 5A

| Molecule # | Alias | Sequence | Length | LNA/DNA |
|---|---|---|---|---|
| M-10518 | 199a_Trunc_LNA_PS_1 | GtagTCtGaACaCtGG | 16 | 9/7 |
| M-11390 | 199a_10293 | GtagTCtgAACaCtGG | 16 | 9/7 |
| M-11391 | 199a_10294 | GTagtCtGaACaCtGG | 16 | 9/7 |
| M-11392 | 199a_10296 | GtagTCtGaACaCTgG | 16 | 9/7 |
| M-11393 | 199a_10683 | GtaGTcTgAAcAcTgG | 16 | 9/7 |

OLIGONUCLEOTIDE-BASED INHIBITORS COMPRISING LOCKED NUCLEIC ACID MOTIF

CROSS-REFERENCE TO RELATED APPLICATIONS

This application claims the benefit of U.S. Provisional Application No. 61/662,746, filed Jun. 21, 2012, and U.S. Provisional Application No. 61/801,533, filed Mar. 15, 2013, both of which are hereby incorporated by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG_036_02US_SeqList_ST25.txt, date recorded Jun. 21, 2013, file size 85 kilobytes).

FIELD OF THE INVENTION

The present invention relates to chemical modification motifs for oligonucleotides, such as antisense oligonucleotides, including mRNA and microRNA (miRNA or miR) inhibitors. The oligonucleotides of the present invention, such as chemically modified antisense oligonucleotides, for example, miRNA antisense oligonucleotides, can have advantages in potency, efficiency of delivery, target specificity, stability, and/or toxicity when administered to a subject.

BACKGROUND OF THE INVENTION

Delivery of oligonucleotides to the body, such as an antisense-based therapeutics, poses several challenges. The binding affinity and specificity to a target, efficiency of cellular uptake, and nuclease resistance are all factors in the delivery and activity of an oligonucleotide-based therapeutic. For example, when oligonucleotides are introduced into intact cells they are attacked and degraded by nucleases leading to a loss of activity. Thus, a useful oligonucleotide should have good resistance to extra- and intracellular nucleases, as well as be able to penetrate the cell membrane.

Polynucleotide analogues have been prepared in an attempt to avoid their degradation, e.g. by means of 2' substitutions (Sproat et al, *Nucleic. Acids Research* 17 (1989), 3373-3386). However, such modifications often affect the polynucleotide's potency for its intended biological action. Such reduced potency may be due to an inability of the modified polynucleotide to form a stable duplex with the target RNA and/or a loss of interaction with the cellular machinery. Other modifications include the use of locked nucleic acids, which has the potential to improve RNA-binding affinity (Veedu and Wengel, *RNA Biology* 6: 3, 321-323 (2009)), however, in vivo efficacy can be low. An oligonucleotide used as an antisense therapeutic should have high affinity for its target to efficiently impair the function of its target (such as inhibiting translation of a mRNA target, or inhibiting the activity of a miRNA target). However, modification of oligonucleotides can decrease its affinity and binding specificity, as well as its ability to impair the function of its target.

Thus, despite the variety of methods described for the delivery of oligonucleotides as a therapeutic, there is a need for improved chemical modifications for stable and efficacious oligonucleotide-based inhibitors.

SUMMARY OF THE INVENTION

The present invention is based, in part, on the discovery that a specific chemical modification pattern or motif of an oligonucleotide can increase the potency, efficiency of delivery, target specificity, stability, and/or improve the toxicity profile when administered to a subject. The present inventors have discovered specific oligonucleotide chemistry modification patterns or motifs with the potential to improve the delivery, stability, potency, specificity, and/or toxicity profile of the oligonucleotide. For example, oligonucleotide chemistry modification patterns or motifs for miRNA inhibitors can improve the delivery, stability, potency, specificity, and/or toxicity profile of the miRNA inhibitor, thus, effectively targeting miRNA function in a therapeutic context.

The present invention provides oligonucleotides with a chemistry modification pattern or motif capable of inhibiting the expression (e.g., abundance) of miRNA with improved properties, such as increased in vivo efficacy. This chemistry modification pattern or motif can be applied to other oligonucleotides for targeting other therapeutic targets, such as mRNA. Thus, the present invention provides a novel therapeutic for the treatment of a variety of diseases, including cardiovascular diseases, obesity, diabetes, and other metabolic disorders.

The oligonucleotide with the specific chemical modification pattern or motif can have an increased in vivo efficacy as compared to an oligonucleotide with the same nucleotide sequence but different chemical modification pattern or motif. For example, an oligonucleotide with a specific locked nucleic acid (LNA) pattern can have an increased in vivo efficacy as compared to an oligonucleotide with the same nucleotide sequence but different LNA pattern.

In one embodiment, the oligonucleotide of the present invention comprises a sequence complementary to the seed region of a miRNA, wherein the sequence comprises at least five LNAs. The oligonucleotide can comprise at least five LNAs complementary to the seed region of a miRNA and at least one non-locked nucleotide. In some embodiments, the non-locked nucleotide is in a region that is complementary to the seed region. The oligonucleotide can have increased in vivo efficacy as compared to a second oligonucleotide comprising the same sequence and LNA composition and different LNA motif. The oligonucleotide can comprise a LNA at the 5' end, 3' end, or both 5' and 3' ends. In some embodiments, the oligonucleotide comprises three or fewer contiguous LNAs. For example, the oligonucleotide comprises no more than three contiguous LNAs. The oligonucleotide can be at least 16 nucleotides in length. In some embodiments, the oligonucleotide can be from 8 to 20 nucleotides in length, from 18 to 50 nucleotides in length, from 10 to 18 nucleotides in length, or from 11 to 16 nucleotides in length. The oligonucleotide in some embodiments is about 8, about 9, about 10, about 11, about 12, about 13, about 14, about 15, about 16, about 17, or about 18 nucleotides in length.

In another embodiment, the oligonucleotide of the present invention comprises a sequence of 16 nucleotides, wherein the sequence comprises at least five LNAs, a LNA at the 5' end, a LNA at the 3' end, and no more than three contiguous LNAs. The oligonucleotide, from the 5' end to the 3' end, can comprise LNAs at positions 1, 5, 6, 8, 10, 11, 13, 15, and 16 of the sequence.

The oligonucleotide described herein can comprise one or more non-locked nucleotides. In some embodiments, at least one of the non-locked nucleotides is 2' deoxy, 2' O-alkyl or 2' halo. In another embodiment, all of the non-locked nucleotides are 2' deoxy, 2' O-alkyl, 2' halo, or any combination thereof.

In some embodiments, the oligonucleotide described herein comprises at least one LNA with a 2' to 4' methylene bridge. The oligonucleotide can have a 5' cap structure, 3' cap structure, or 5' and 3' cap structure. In some embodiments, the oligonucleotide comprises one or more phosphorothioate linkages or is fully phosphorothioate-linked. The oligonucleotide can have one to three phosphate linkages. The oligonucleotide can further comprise a pendent lipophilic or hydrophilic group.

In one embodiment, the oligonucleotide is an inhibitor of a RNA, such as an inhibitor of its expression or activity. In one embodiment, the oligonucleotide is a miRNA inhibitor. For example, the oligonucleotide can comprise a sequence that is substantially or completely complementary to a nucleotide sequence of a miRNA or fragment thereof. The miRNA can be expressed in any tissue, or selectively expressed in a tissue. In one embodiment, the tissue is cardiac tissue. For example, the miRNA is selectively expressed in cardiac tissue.

The oligonucleotide can be an inhibitor of any miRNA. In some embodiments, the oligonucleotide can be an inhibitor of any miRNA, but not miR-208a, miR-208b, or miR-499. Such inhibitors are described in, for example. International Publication No. WO 2012/083005, which is hereby incorporated by reference in its entirety. In one embodiment, the oligonucleotide is an inhibitor of a miR selected from Table 1 or Table 2. In yet another embodiment, the oligonucleotide is an inhibitor of miR-15a, miR-15b, miR-16-1, miR-16-2, miR-24, miR-25, miR-26a, miR-497, miR-195, miR-424, a let 7 family member, miR-21, miR-199a-b, miR-214, miR-10a-b, miR-16, miR-125b, miR-146a-b, miR-221, miR-222, a miR-30 family member, miR-126, miR-133, miR-1, miR-143, miR-145, miR-486, miR-92a, miR-320, miR-1-1, miR-1-2, miR-451, miR-378, miR-378*, miR-92, miR-34a, miR-34b, miR-34c, miR-29, or miR-33.

In yet another embodiment, the oligonucleotide can be an inhibitor of mRNA. For example, the sequence can be substantially or completely complementary to a nucleotide sequence of an mRNA or fragment thereof.

Also provided herein is a pharmaceutical composition comprising an effective amount of the oligonucleotide described herein, or a pharmaceutically-acceptable salt thereof, and a pharmaceutically-acceptable carrier or diluent. In some embodiments, the pharmaceutically-acceptable carrier can comprise a colloidal dispersion system, macromolecular complex, nanocapsule, nanoparticle, microsphere, bead, oil-in-water emulsion, micelle, mixed micelle, or liposome. In another embodiment, the pharmaceutically-acceptable carrier or diluent consists essentially of saline.

The present invention also provides methods of producing and using an oligonucleotide described herein. A method of reducing or inhibiting activity of a miRNA in a cell comprising contacting the cell with an oligonucleotide described herein is also provided. Also disclosed herein is a method of reducing expression of an mRNA in a cell comprising contacting the cell with an oligonucleotide disclosed herein. The cell can be any cell type, such as a heart cell. The cell can be in vivo or ex vivo. In one embodiment, the cell is a mammalian cell.

A method of preventing or treating a condition in a subject associated with or mediated by expression of an RNA is also provided. The method can comprise administering to the subject a pharmaceutical composition comprising an oligonucleotide disclosed herein. In one embodiment, a method of preventing or treating a condition in a subject associated with or mediated by the activity of a miRNA comprises administering to the subject a pharmaceutical composition comprising the oligonucleotide disclosed herein. In another embodiment, a method of preventing or treating a condition in a subject associated with or mediated by the activity of a mRNA comprises administering to the subject a pharmaceutical composition comprising the oligonucleotide disclosed herein. The condition can be a heart condition, such as pathologic cardiac hypertrophy, myocardial infarction, myocardial ischemia, ischemia-reperfusion injury, cardiomyopathy, or heart failure. The pharmaceutical composition can be administered by parenteral administration, such as by intravenous, subcutaneous, intraperitoneal, or intramuscular administration. In some embodiments, administration is by direct injection into cardiac tissue. In yet in some embodiments, the composition is administered by oral, transdermal, sustained release, controlled release, delayed release, suppository, catheter, or sublingual administration. Furthermore, the subject can be a human. In some embodiments, an oligonucleotide disclosed herein is delivered at a dose of between about 10 mg/kg to about 100 mg/kg, between about 10 mg/kg to about 50 mg/kg, between about 10 mg/kg to about 25 mg/kg. In some embodiments, an oligonucleotide disclosed herein is delivered at a dose of about 100 mg/kg or less, about 50 mg/kg or less, about 25 mg/kg or less, or about 10 mg/kg or less. In one embodiment, the oligonucleotide is formulated in saline and administered subcutaneously.

DETAILED DESCRIPTION OF THE INVENTION

Figure 1B:
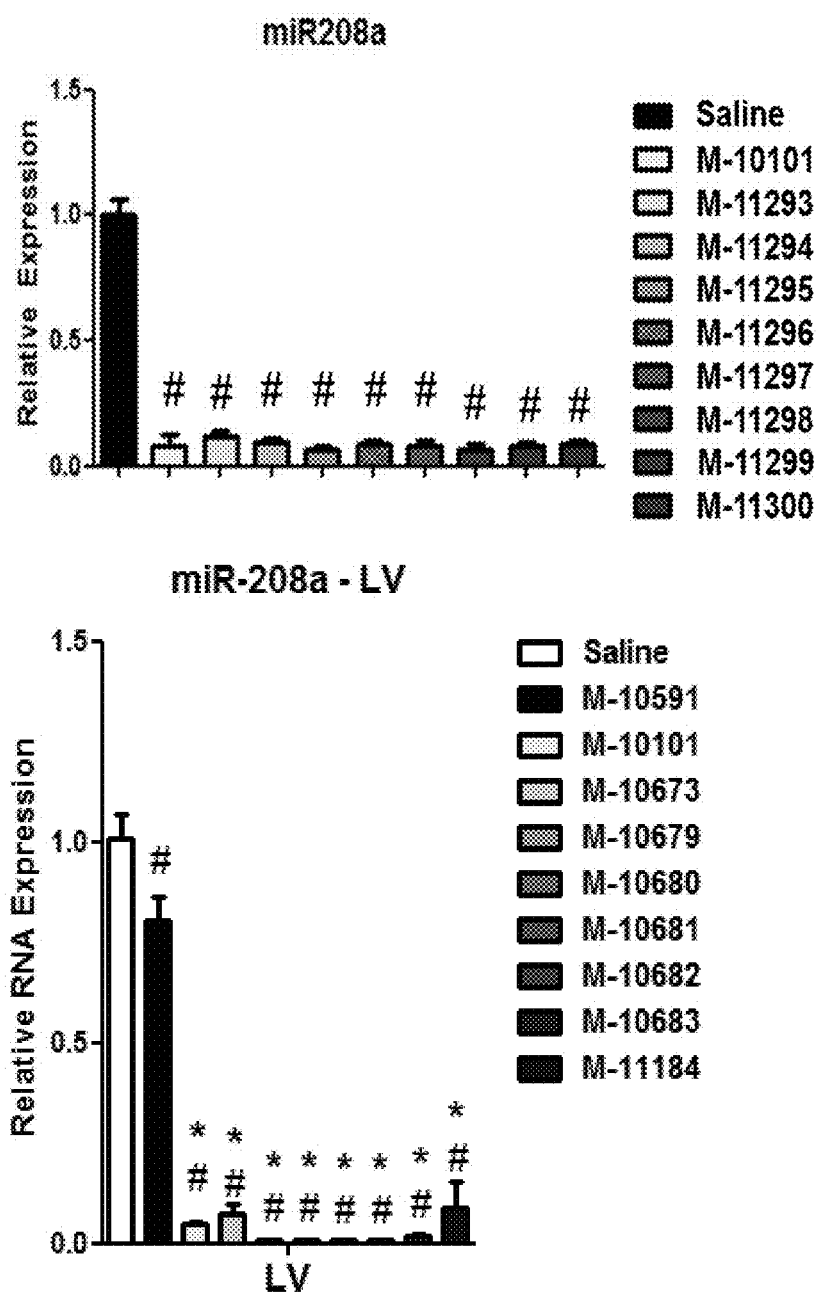
FIG. 1. (A) Location of LNA and DNA bases for 16 antimiRs designed to target miR-208a (SEQ ID NOs: 76-91). LNA bases are represented by a capital letter. DNA bases are represented by a lower case letter. (B) MiR-208a inhibition by antimiR-208a compounds. All antimiR compounds showed significant inhibition in the left ventricle. #$p<0.05$ vs Saline. *$p<0.05$ vs. control oligo, M-10591. (C) Real-time PCR from cardiac tissue of antimiR-208a-treated rats showed differing target de-repression in vivo using Dynlt1 as a primary readout for efficacy and target de-repression. #$p<0.05$ vs Saline. *$p<0.05$ vs. control oligo, M-10591. (D) Serum levels of toxicology parameters. Four days after injection, plasma was collected from all groups. No antimiR-208a oligonucleotide or control oligonucleotide showed increased levels of liver toxicity as assessed by ALT and AST measurements, or kidney toxicity as assessed by BUN measurements compared to saline controls. (E) Quantification of antimiR from heart, liver, and kidney four days after a single 25 mg/kg subcutaneous dose. Distribution to the heart is much lower than liver and kidney. Efficacious compounds are not more robustly distributed to the heart.

The present invention is based, in part, on the discovery that a specific chemical modification pattern or motif of an oligonucleotide can improve the potency, efficiency of delivery, target specificity, stability, and/or toxicity when administered to a subject. The oligonucleotide with the specific chemical modification pattern or motif can have an increased in vivo efficacy as compared to an oligonucleotide with the same nucleotide sequence but different chemical modification pattern or motif. For example, an oligonucleotide with a specific LNA/DNA pattern can have an increased in vivo efficacy as compared to an oligonucleotide with the same nucleotide sequence but different LNA/DNA pattern.

The invention provides in some embodiments, oligonucleotides capable of inhibiting, in a specific fashion, the expression or abundance of an RNA species, such as a miRNA or mRNA. The invention further provides pharmaceutical compositions comprising the oligonucleotides, and methods of treating patients having conditions or disorders relating to or involving the RNA, such as miRNA or mRNA, such as a various cardiovascular conditions. In various embodiments, the oligonucleotides provide advantages in one or more of potency, efficiency of delivery, target specificity, toxicity, and/or stability.

In one aspect, the present invention provides an oligonucleotide capable of reducing the expression or abundance of an RNA, such as a mRNA or miRNA. The oligonucleotide of the present invention may have increased in vivo efficacy as compared to another oligonucleotide with the same nucleotide sequence but different chemical modification motif or pattern. For example, a first and a second oligonucleotide each have the same nucleotide sequence that targets a miRNA. The first oligonucleotide has a chemical modification motif or pattern that differs from the second oligonucleotide. Both the first and second oligonucleotides are capable of reducing the expression or abundance of a miRNA. However, the first oligonucleotide with a first chemical modification motif has a higher in vivo efficacy as compared to the second oligonucleotide with a different chemical modification motif, as measured by the amount of de-repression of one or more of the miRNA's targets.

The activity of the oligonucleotide in reducing the expression or abundance of an RNA species, such as miRNA, may be determined in vitro and/or in vivo. For example, when inhibition of a miRNA activity is determined in vitro, the activity may be determined using a dual luciferase assay, such as that described herein. The oligonucleotide significantly inhibits such activity, as determined in the dual luciferase activity, at a concentration of about 50 nM or less, or in other embodiments, 40 nM or less, 20 nM or less, or 10 nM or less. For example, the oligonucleotide may have an IC50 for inhibition of a miRNA activity of about 50 nM or less, about 40 nM or less, about 30 nM or less, or about 20 nM or less, as determined in the dual luciferase assay. The dual luciferase assay, as exemplified by the commercially available product PsiCHECK™ (Promega), involves placement of the miR recognition site in the 3' UTR of a gene for a detectable protein (e.g., renilla luciferase). The construct is co-expressed with the target miRNA, such that inhibitor activity can be determined by change in signal. A second gene encoding a detectable protein (e.g., firefly luciferase) can be included on the same plasmid, and the ratio of signals determined as an indication of antimiR activity.

Alternatively, or in addition, the activity of the oligonucleotide in reducing the expression or abundance of an RNA species, such as miRNA, may be determined in a suitable mouse or rat model, such as those described herein, where inhibition (e.g., by at least 50%) of a miRNA is observed at an oligonucleotide dose, such as a dose of about 50 mg/kg or less, about 25 mg/kg or less, about 10 mg/kg or less or about 5 mg/kg or less. In some embodiments, the activity of the oligonucleotide is determined in an animal model, such as described in WO 2008/016924, which descriptions are hereby incorporated by reference. For example, the oligonucleotide may exhibit at least 50% target miRNA inhibition, such as a dose of about 50 mg/kg or less, about 25 mg/kg or less, such as about 10 mg/kg or less or about 5 mg/kg or less. In such embodiments, the oligonucleotide may be dosed intravenously or subcutaneously to mice, and the oligonucleotide may be formulated in saline.

The in vivo efficacy of the oligonucleotide may be determined by assessing the level or amount of de-repression of one or more of the miRNA's targets in a suitable mouse or rat model, such as those described herein. The oligonucleotide may exhibit at least 50% target de-repression at a dose of about 50 mg/kg or less, about 25 mg/kg or less, about 10 mg/kg or less or about 5 mg/kg or less. In such embodiments, the oligonucleotide may be dosed intravenously or subcutaneously to mice, and the oligonucleotide may be formulated in saline.

In these or other embodiments, the oligonucleotides of the present invention can be stable after administration, being detectable in the circulation and/or target organ for at least three weeks, at least four weeks, at least five weeks, or at least six weeks, or more, following administration. Thus, the oligonucleotides of the present invention may provide for less frequent administration, lower doses, and/or longer duration of therapeutic effect.

The nucleotide sequence of the oligonucleotide can be substantially complementary to a nucleotide sequence of a RNA, such as a mRNA or miRNA. In some embodiments, the miRNA is not miR-208a, miR-208b, or miR-499. The oligonucleotide comprises at least one LNA, such as at least five, at least seven or at least nine LNAs. In some embodiments, the oligonucleotide comprises a mix of LNA and non-locked nucleotides. For example, the oligonucleotide may contain at least five or at least seven or at least nine locked nucleotides, and at least one non-locked nucleotide.

Generally, the length of the oligonucleotide and number and position of locked nucleotides is such that the oligonucleotide reduces RNA expression or abundance, such as mRNA expression or miRNA expression, at an oligonucleotide concentration of about 50 nM or less in the in vitro luciferase assay, or at a dose of about 50 mg/kg or less, or about 25 mg/kg or less in a suitable mouse or rat model, each as described herein. In some embodiments, the oligonucleotide is a miRNA inhibitor, such that the length of the oligonucleotide and number and position of locked nucleotides is such that the oligonucleotide reduces miRNA activity as determined by target de-repression, at a dose of about 50 mg/kg or less, or about 25 mg/kg or less in a suitable mouse or rat model, such as those described herein.

The oligonucleotide of the present invention can comprise a sequence of nucleotides in which the sequence comprises at least five LNAs, a LNA at the 5' end of the sequence, a LNA at the 3' end of the sequence, or any combination thereof. In one embodiment, the oligonucleotide comprises a sequence of nucleotides in which the sequence comprises at least five LNAs, a LNA at the 5' end of the sequence, a LNA at the 3' end of the sequence, or any combination thereof, wherein three or fewer of the nucleotides are contiguous LNAs. For example, the oligonucleotide comprises no more than three contiguous LNAs. For example, the oligonucleotide may comprise a sequence with at least five LNAs, a LNA at the 5' end, a LNA at the 3' end, and no more than three contiguous LNAs. The oligonucleotide may comprise a sequence with at least five LNAs, a LNA at the 5' end, a LNA at the 3' end, and no more than three contiguous LNAs, wherein the sequence is at least 16 nucleotides in length. The sequence can be substantially or completely complementary to a RNA, such as mRNA, or miRNA, wherein a substantially complementary sequence may have from 1 to 4 mismatches (e.g., 1 or 2 mismatches) with respect to its target sequence. In one embodiment, the target sequence is a miRNA, such that the oligonucleotide is a miRNA inhibitor, or antimiR. The miRNA can be any miRNA, such as, but not limited to, those listed in Table 1 or Table 2. Exemplary miRNA therapeutic utilities are disclosed in the US and PCT patent references listed in Table 2 below, each of which is hereby incorporated by reference in its entirety. The mature and pre-processed forms of miRNAs are disclosed in the patent references listed in Table 2, and such descriptions are also hereby incorporated by reference.

TABLE 1

| miRNA | miRNA Sequence | SEQ ID NO: |
|---|---|---|
| 1 | UGGAAUGUAAAGAAGUAUGUAU | 1 |
| 100 | AACCCGUAGAUCCGAACUUGUG | 2 |
| 10a | UACCCUGUAGAUCCGAAUUUGUG | 3 |
| 10b | UACCCUGUAGAACCGAAUUUGUG | 4 |
| 125b | UCCCUGAGACCCUAACUUGUGA | 5 |
| 126 | UCGUACCGUGAGUAAUAAUGCG | 6 |
| 128 | UCACAGUGAACCGGUCUCUUU | 7 |
| 133a | UUUGGUCCCCUUCAACCAGCUG | 8 |
| 133b | UUUGGUCCCCUUCAACCAGCUA | 9 |
| 139 | UCUACAGUGCACGUGUCUCCAG | 10 |
| 143 | UGAGAUGAAGCACUGUAGCUC | 11 |
| 145 | GUCCAGUUUUCCCAGGAAUCCCU | 12 |
| 146a | UGAGAACUGAAUUCCAUGGGUU | 13 |
| 146b | UGAGAACUGAAUUCCAUAGGCU | 14 |
| 150 | UCUCCCAACCCUUGUACCAGUG | 15 |
| 15a | UAGCAGCACAUAAUGGUUUGUG | 16 |
| 15b | UAGCAGCACAUCAUGGUUUACA | 17 |
| 16 | UAGCAGCACGUAAAUAUUGGCG | 18 |
| 181b | AACAUUCAUUGCUGUCGGUGGGU | 19 |
| 195 | UAGCAGCACAGAAAUAUUGGC | 20 |
| 197 | UUCACCACCUUCUCCACCCAGC | 21 |
| 199a | CCCAGUGUUCAGACUACCUGUUC | 22 |
| 199b-5p | CCCAGUGUUUAGACUAUCUGUUC | 23 |
| 199b-3p | ACAGUAGUCUGCACAUUGGUUA | 24 |
| 208a | AUAAGACGAGCAAAAAGCUUGU | 25 |
| 208b | AUAAGACGAACAAAAGGUUUGU | 26 |
| 20a | UAAAGUGCUUAUAGUGCAGGUAG | 27 |
| 21 | UAGCUUAUCAGACUGAUGUUGA | 28 |
| 214 | ACAGCAGGCACAGACAGGCAGU | 29 |
| 22 | AAGCUGCCAGUUGAAGAACUGU | 30 |
| 221 | AGCUACAUUGUCUGCUGGGUUUC | 31 |
| 222 | AGCUACAUCUGGCUACUGGGU | 32 |
| 224 | CAAGUCACUAGUGGUUCCGUU | 33 |
| 23a | AUCACAUUGCCAGGGAUUUCC | 34 |
| 24 | UGGCUCAGUUCAGCAGGAACAG | 35 |
| 25 | CAUUGCACUUGUCUCGGUCUGA | 36 |
| 26a | UUCAAGUAAUCCAGGAUAGGCU | 37 |
| 26b | UUCAAGUAAUUCAGGAUAGGU | 38 |
| 28 | AAGGAGCUCACAGUCUAUUGAG | 39 |
| 29a | UAGCACCAUCUGAAAUCGGUUA | 40 |
| 29b | UAGCACCAUUUGAAAUCAGUGUU | 41 |

TABLE 1 -continued

| miRNA | miRNA Sequence | SEQ ID NO: |
|---|---|---|
| 29c | UAGCACCAUUUGAAAUCGGUUA | 42 |
| 30a | UGUAAACAUCCUCGACUGGAAG | 43 |
| 30b | UGUAAACAUCCUACACUCAGCU | 44 |
| 30c | UGUAAACAUCCUACACUCUCAGC | 45 |
| 30d | UGUAAACAUCCCCGACUGGAAG | 46 |
| 30e | UGUAAACAUCCUUGACUGGAAG | 47 |
| 33a | GUGCAUUGUAGUUGCAUUGCA | 48 |
| 33b | GUGCAUUGCUGUUGCAUUGC | 49 |
| 34a | UGGCAGUGUCUUAGCUGGUUGU | 50 |
| 34b | CAAUCACUAACUCCACUGCCAU | 51 |
| 34c | AGGCAGUGUAGUUAGCUGAUUGC | 52 |
| 320 | AAAAGCUGGGUUGAGAGGGCGA | 53 |
| 342-3p | UCUCACACAGAAAUCGCACCCGU | 54 |
| 382 | GAAGUUGUUCGUGGUGGAUUCG | 55 |
| 422a | ACUGGACUUAGGGUCAGAAGGC | 56 |
| 378 | ACUGGACUUGGAGUCAGAAGG | 57 |
| 378* | CUCCUGACUCCAGGUCCUGUGU | 58 |
| 424 | CAGCAGCAAUUCAUGUUUUGAA | 59 |
| 451 | AAACCGUUACCAUUACUGAGUU | 60 |
| 483-3p | UCACUCCUCUCCUCCCGUCUU | 61 |
| 484 | UCAGGCUCAGUCCCCUCCCGAU | 62 |
| 486-5p | UCCUGUACUGAGCUGCCCCGAG | 63 |
| 497 | CAGCAGCACACUGUGGUUUGU | 64 |
| 499 | UUAAGACUUGCAGUGAUGUUU | 65 |
| 542-5p | UCGGGGAUCAUCAUGUCACGAGA | 66 |
| 92a | UAUUGCACUUGUCCCGGCCUGU | 67 |
| 92b | UAUUGCACUCGUCCCGGCCUCC | 68 |
| let-7a | UGAGGUAGUAGGUUGUAUAGUU | 69 |
| let-7b | UGAGGUAGUAGGUUGUGUGGUU | 70 |
| let-7c | UGAGGUAGUAGGUUGUAUGGUU | 71 |
| let-7d | AGAGGUAGUAGGUUGCAUAGUU | 72 |
| let-7e | UGAGGUAGGAGGUUGUAUAGUU | 73 |
| let-7f | UGAGGUAGUAGAUUGUAUAGUU | 74 |
| let-7g | UGAGGUAGUAGUUUGUACAGUU | 75 |

TABLE 2

| miRNA | Indications | Reference |
|---|---|---|
| miR-208a/miR-208b/miR-499 | Pathologic cardiac hypertrophy, myocardial infarction, heart failure | WO 2008/016924 (208a) WO 2009/018492 (208b/499) |
| miR-208a/miR-208b | Metabolic Disorders (obesity, hyperlipidemia, diabetes, metabolic syndrome, hypercholesterolemia; hepatic steatosis) | PCT/US2012/059349, filed Oct. 9, 2012 |
| miR-15/miR-16/miR-195 | Pathologic cardiac hypertrophy, myocardial infarction, heart failure | WO 2009/062169 |
| miR-29 | Profibrotic agents to convert soft plaques (vulnerable plaques) to fibrotic tissue; induce collagen deposition | WO 2009/018493 |
| miR-126 | Pathologic vascularization | WO 2010/019574 |
| miR-145 | Muscle injury | WO 2007/070483 |
| miR-1/miR-133 | Muscle injury (antagonist/agonist of each miRNA applied in combination at different times) | WO 2007/070483 |
| miR-451 | Polycythemia | WO 2012/148373 |
| miR-378/miR-378* | Metabolic disorders (obesity, hyperlipidemia, diabetes, metabolic syndrome, hypercholesterolemia; hepatic steatosis); Pathologic cardiac hypertrophy, myocardial infarction, heart failure | WO 2011/153542 |
| miR-92 | Promotes angiogenesis and vessel repair | US 2010/0324118 A1 |
| miR-34a | Myocardial infarction | US 2012/0238619 A1 |
| miR-145 | Pulmonary arterial hypertension | WO 2012/153135 |
| miR-33 | Statin-induced hepatotoxicity, cholestasis, increasing HDL cholesterol | US 20110281933 A1 |

In some embodiments, the oligonucleotide comprises a sequence that is substantially or completely complementary to a miRNA that is selected from the group consisting of, but not limited to: miR-15a, miR-15b, miR-16-1, miR-16-2, miR-24, miR-25, miR-26a, miR-497, miR-195, miR-424, a let 7 family member, miR-21, miR-199a-b, miR-214, miR-10a-b, miR-16, miR-125b, miR-146a-b, miR-221, miR-222, a miR-30 family member, miR-126, miR-133, miR-1, miR-143, miR-145, miR-486, miR-92a, miR-320, miR-1-1, miR-1-2, miR-451, miR-378, miR-378*, miR-92, miR-34a, miR-34b, miR-34c, miR-29, or miR-33. In some embodiments, the miRNA is not miR208a, miR208b, or miR-499, such as described in International Publication No. WO 2012/083005, which is hereby incorporated by reference in its entirety. In some embodiments, the miRNA is expressed in a specific tissue, such as kidney, liver, or cardiac tissue. In yet another embodiment, the miRNA is selectively expressed in a tissue, such as kidney, liver, or cardiac tissue.

In yet another embodiment, the oligonucleotide of the present invention can comprise a sequence complementary to the seed region of a miRNA, wherein the sequence comprises at least five LNAs. The "seed region of a miRNA" is the portion spanning bases 2 to 9 at the 5' end of the miRNA. The miRNA can be any miRNA, such as, but not limited to those listed in Table 1 or Table 2. The miRNA can be, but is not limited to: miR-1.5a, miR-15b, miR-16-1, miR-16-2, miR-24, miR-25, miR-26a, miR-497, miR-195, miR-424, a let 7 family member, miR-21, miR-199a-b, miR-214, miR-10a-b, miR-16, miR-125b, miR-146a-b, miR-221, miR-222, a miR-30 family member, miR-126, miR-133, miR-1, miR-143, miR-145, miR-486, miR-92a, miR-320, miR-1-1, miR-1-2, miR-451, miR-378, miR-378*, miR-92, miR-34a, miR-34b, miR-34c, miR-29, or miR-33. In some embodiments, the miRNA is not miR208a, miR208b, or miR-499. The sequence can be substantially or completely complementary to the miRNA. In some embodiments, the miRNA is expressed in a specific tissue, such as kidney, liver, or cardiac tissue. In yet another embodiment, the miRNA is selectively expressed in a tissue, such as kidney, liver, or cardiac tissue. In some embodiments, the miRNA is selectively expressed in a particular cell type, including, but not limited to, cardiomyocytes, myocytes, fibroblasts, smooth muscle cells, endothelial cells, and monocytes.

The oligonucleotide comprising a sequence complementary to the seed region of a miRNA, wherein the sequence comprises at least five LNAs, may comprise a LNA at the 5' end or a LNA at the 3' end, or both a LNA at the 5' end and 3' end. In one embodiment, the oligonucleotide comprising at least 5 LNAs, a LNA at the 5' end and/or a LNA at the 3' end, also has three or fewer consecutive LNAs. In some embodiments, the sequence is at least 16 nucleotides in length. The sequence complementary to the seed region of a miRNA can be substantially complementary or completely complementary.

The oligonucleotide of the present invention contains one or more locked nucleic acid (LNAs) residues, or "locked nucleotides." LNAs are described, for example, in U.S. Pat. Nos. 6,268,490; 6,316,198; 6,403,566; 6,770,748; 6,998,484; 6,670,461; and 7,034,133, all of which are hereby incorporated by reference in their entireties. LNAs are modified nucleotides or ribonucleotides that contain an extra bridge between the 2' and 4' carbons of the ribose sugar moiety resulting in a "locked" conformation, and/or bicyclic structure. In one embodiment, the oligonucleotide contains one or more LNAs having the structure shown by structure A below. Alternatively or in addition, the oligonucleotide may contain one or more LNAs having the structure shown by structure B below. Alternatively or in addition, the oligonucleotide contains one or more LNAs having the structure shown by structure C below.

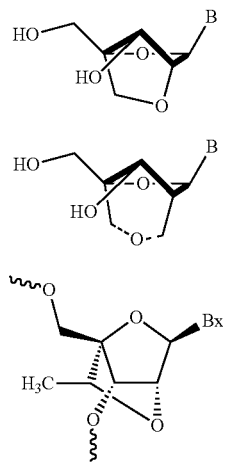

Other suitable locked nucleotides that can be incorporated in the oligonucleotides of the present invention include those described in U.S. Pat. Nos. 6,403,566 and 6,833,361, both of which are hereby incorporated by reference in their entireties.

In exemplary embodiments, the locked nucleotides have a 2' to 4' methylene bridge, as shown in structure A, for example. In other embodiments, the bridge comprises a methylene or ethylene group, which may be substituted, and which may or may not have an ether linkage at the 2' position.

The oligonucleotide may comprise, consist essentially of, or consist of, an antisense sequence to a mRNA or miRNA. In one embodiment, the oligonucleotide comprises an antisense sequence directed to a miRNA. For example, the oligonucleotide comprises an antisense sequence that is sufficiently complementary to a miRNA sequence to hybridize to the endogenous miRNA under physiological conditions. In such embodiments, the oligonucleotide can comprise a sequence that is at least partially complementary to a mature miRNA sequence, e.g. at least about 75%, about 80%, about 85%, about 90%, about 95%, about 96%, about 97%, about 98%), or about 99% complementary to a mature miRNA sequence, such as, but not limited to, a miRNA in Table 1, Table 2, or any one of the following miRNAs: miR-15a, miR-15b, miR-16-1, miR-16-2, miR-24, miR-25, miR-26a, miR-497, miR-195, miR-424, a let 7 family member, miR-21, miR-199a-b, miR-214, miR-10a-b, miR-16, miR-125b, miR-146a-b, miR-221, miR-222, a miR-30 family member, miR-126, miR-133, miR-1, miR-143, miR-145, miR-486, miR-92a, miR-320, miR-1-1, miR-1-2, miR-451, miR-378, miR-378*, miR-92, miR-34a, miR-34b, miR-34c, miR-29, or miR-33. In some embodiments, the miRNA is not miR208a, miR208b, or miR-499. In one embodiment, the antisense oligonucleotide comprises a sequence that is 100% complementary to a mature miRNA sequence, such as, but not limited to, a miRNA selected from the group consisting of miR-15a, miR-15b, miR-16-1, miR-16-2, miR-24, miR-25, miR-26a, miR-497, miR-195, miR-424, a let 7 family member, miR-21, miR-199a-b, miR-214, miR-10a-b, miR-16, miR-125b, miR-146a-b, miR-221, miR-222, a miR-30 family member, miR-126, miR-133, miR-1, miR-143, miR-145, miR-486, miR-92a, miR-320, miR-1-1, miR-1-2, miR-451, miR-378, miR-378*, miR-92, miR-34a, miR-34b, miR-34c, miR-29, or miR-33. In some embodiments, the miRNA is not miR208a, miR208b, or miR-499. In some embodiments, the miRNA is not miR-208a, miR-208b, or miR-499.

The oligonucleotide generally has a nucleotide sequence designed to target mature miRNA. The oligonucleotide may, in these or other embodiments, also or alternatively be designed to target the pre- or pri-miRNA forms. In certain embodiments, the oligonucleotide may be designed to have a sequence containing from 1 to 5 (e.g., 1, 2, 3, or 4) mismatches relative to the fully complementary (mature) miRNA sequence. In some embodiments, the miRNA is not miR-208a, miR-208b, or miR-499. In certain embodiments, such antisense sequences may be incorporated into shRNAs or other RNA structures containing stem and loop portions, for example.

In certain embodiments, the oligonucleotide comprises a nucleotide sequence that is completely complementary (i.e. fully complementary) to a nucleotide sequence of a miRNA. In some embodiments, the miRNA is not miR-208a, miR-208b, or miR-499. In particular embodiments, the oligonucleotide comprises, consists essentially of, or consists of a sequence completely complementary to the nucleotide sequence of a miRNA. In this context, "consists essentially of" includes the optional addition of nucleotides (e.g., one or two) on either or both of the 5' and 3' ends, so long as the additional nucleotide(s) do not substantially affect (as defined by an increase in IC50 of no more than 20%) the oligonucleotide's inhibition of the target miRNA activity in the dual luciferase assay or mouse model.

The oligonucleotide can be from about 8 to about 20 nucleotides in length, from about 18 to about 50 nucleotides in length, from about 10 to about 18 nucleotides in length, or from about 11 to about 16 nucleotides in length. The oligonucleotide in some embodiments is about 8, about 9, about 10, about 11, about 12, about 13, about 14, about 15, about 16, about 17, or about 18 nucleotides in length. In some embodiments, the oligonucleotide is at least 16 nucleotides in length.

The oligonucleotide generally contains at least about 5, at least about 7, or at least about 9 LNAs, but in various embodiments is not fully comprised of LNAs. Generally, the number and position of LNAs is such that the oligonucleotide reduces mRNA or miRNA activity. In one embodiment, the number and position of LNAs is such that the oligonucleotide has increased in vivo efficacy as compared to an oligonucleotide with a different number and/or position of LNAs. In certain embodiments, the oligonucleotide does not contain a stretch of nucleotides with more than four, or more than three, contiguous LNAs. For example, the oligonucleotide comprises no more than three contiguous LNAs. In these or other embodiments, the oligonucleotide can comprise a region or sequence that is substantially or completely complementary to a miRNA seed region, in which the region or sequence comprises at least three, at least four, or at least five locked nucleotides. In some embodiments, the miRNA is not miR-208a, miR-208b, or miR-499.

In various embodiments, the oligonucleotide contains at least nine locked nucleotides. For example, the oligonucleotide may contain nine locked nucleotides and seven non-locked nucleotides. The pattern of LNAs may be such that, from the 5' end to the 3' end of the oligonucleotide, at least positions 1, 6, 10, 13, and 15 are LNAs. In some embodiments, the pattern of LNAs may be such that, from the 5' end to the 3' end of the oligonucleotide, at least positions 1, 6, 10, 11, 13, and 16 are LNAs. In certain embodiments, from the 5' end to the 3' end of the oligonucleotide, positions 1, 5, 6, 8, 10, 11, 13, 15, and 16 are LNAs, and the remaining positions are non-locked nucleotides. In some embodiments, from the 5' end to the 3' end of the oligonucleotide, positions 1, 4, 5, 7, 9, 10, 12, 14, and 16 are LNAs, and remaining positions are non-locked nucleotides. For example, in one embodiment, an oligonucleotide can comprise at least 16 nucleotides, in which from the 5' end to the 3' end of the oligonucleotide, positions 1, 5, 6, 8, 10, 11, 13, 15, and 16 are LNAs, and the remaining positions are non-locked nucleotides, wherein the oligonucleotide is a miRNA inhibitor.

For example, the oligonucleotide can comprise at least 16 nucleotides, in which from the 5' end to the 3' end of the oligonucleotide, positions 1, 5, 6, 8, 10, 11, 13, 15, and 16 are LNAs, and the remaining positions are non-locked nucleotides, the oligonucleotide is at least partially complementary to a miRNA, in which the miRNA may in some embodiments, not be miR-208a, miR-208b, or miR-499. In another embodiment, the oligonucleotide can comprise at least 16 nucleotides, in which from the 5' end to the 3' end of the oligonucleotide, positions 1, 5, 6, 8, 10, 11, 13, 14, and 16 are LNAs, and the remaining positions are non-locked nucleotides, the oligonucleotide is at least partially complementary to a miRNA, in which the miRNA may in some embodiments, not be miR-208a, miR-208b, or miR-499. In yet another example, the oligonucleotide can comprise at least 16 nucleotides, in which from the 5' end to the 3' end of the oligonucleotide, positions 1, 5, 6, 8, 10, 11, 13, 15, and 16 are LNAs, and the remaining positions are non-locked nucleotides, the oligonucleotide is at least partially complementary to a seed region of a miRNA, in which the miRNA may in some embodiments, not be miR-208a, miR-208b, or miR-499. In some embodiments, the oligonucleotide is selected from Tables 3, 5, 6, 7, 8, or 9. In certain embodiments, the oligonucleotide is a compound selected from M-10101, M-10707, M-11192, M-11185, M-10518, or M-11127.

For non-locked nucleotides, the nucleotide may contain a T modification with respect to a 2' hydroxyl. For example, the 2' modification may be 2' deoxy. Incorporation of 2'-modified nucleotides in antisense oligonucleotides may increase both resistance of the oligonucleotides to nucleases and their thermal stability with complementary RNA. Various modifications at the 2' positions may be independently selected from those that provide increased nuclease sensitivity, without compromising molecular interactions with the RNA target or cellular machinery. Such modifications may be selected on the basis of their increased potency in vitro or in vivo. Exemplary methods for determining increased potency (e.g., IC50) for miRNA inhibition are described herein, including the dual luciferase assay and in vivo miRNA expression or target de-repression.

In some embodiments the 2' modification may be independently selected from O-alkyl (which may be substituted), halo, and deoxy (H). Substantially all, or all, nucleotide 2' positions of the non-locked nucleotides may be modified in certain embodiments, e.g., as independently selected from O-alkyl (e.g., O-methyl), halo (e.g., fluoro), deoxy (H), and amino. For example, the 2' modifications may each be independently selected from O-methyl and fluoro. In exemplary embodiments, purine nucleotides each have a 2' OMe and pyrrolidine nucleotides each have a 2'-F. In certain embodiments, from one to about five 2' positions, or from about one to about three 2' positions are left unmodified (e.g., as 2' hydroxyls).

2' modifications in accordance with the invention also include small hydrocarbon substituents. The hydrocarbon substituents include alkyl, alkenyl, alkynyl, and alkoxyalkyl, where the alkyl (including the alkyl portion of alkoxy), alkenyl and alkynyl may be substituted or unsubstituted. The alkyl, alkenyl, and alkynyl may be C1 to C10 alkyl, alkenyl or alkynyl, such as C1, C2, or C3. The hydrocarbon substituents may include one or two or three non-carbon atoms, which may be independently selected from N, O, and/or S. The 2' modifications may further include the alkyl, alkenyl, and alkynyl as O-alkyl, O-alkenyl, and O-alkynyl.

Exemplary 2' modifications in accordance with the invention include 2'-O-alkyl (C1-3 alkyl, such as 2'OMe or 2'OEt), 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) substitutions.

In certain embodiments, the oligonucleotide contains at least one 2'-halo modification (e.g., in place of a 2' hydroxyl), such as 2'-fluoro, 2'-chloro, 2'-bromo, and 2'-iodo. In some embodiments, the 2' halo modification is fluoro. The oligonucleotide may contain from 1 to about 5 2'-halo modifications (e.g., fluoro), or from 1 to about 3 2'-halo modifications (e.g., fluoro). In some embodiments, the oligonucleotide contains all 2'-fluoro nucleotides at non-locked positions, or 2'-fluoro on all non-locked pyrimidine nucleotides. In certain embodiments, the 2'-fluoro groups are independently di-, tri-, or un-methylated.

The oligonucleotide may have one or more 2'-deoxy modifications (e.g., H for 2' hydroxyl), and in some embodiments, contains from 2 to about 10 2'-deoxy modifications at non-locked positions, or contains 2'deoxy at all non-locked positions.

In exemplary embodiments, the oligonucleotide contains 2' positions modified as 2'OMe in non-locked positions. Alternatively, non-locked purine nucleotides are modified at the 2' position as 2'OMe, with non-locked pyrimidine nucleotides modified at the 2' position as 2'-fluoro.

In certain embodiments, the oligonucleotide further comprises at least one terminal modification or "cap". The cap may be a 5' and/or a 3'-cap structure. The terms "cap" or "end-cap" include chemical modifications at either terminus of the oligonucleotide (with respect to terminal ribonucleotides), and including modifications at the linkage between the last two nucleotides on the 5' end and the last two nucleotides on the 3' end. The cap structure as described herein may increase resistance of the oligonucleotide to exonucleases without compromising molecular interactions with the RNA target or cellular machinery. Such modifications may be selected on the basis of their increased potency in vitro or in vivo. The cap can be present at the 5'-terminus (5'-cap) or at the 3'-terminus (3'-cap) or can be present on both ends. In certain embodiments, the 5'- and/or 3'-cap is independently selected from phosphorothioate monophosphate, abasic residue (moiety), phosphorothioate linkage, 4'-thio nucleotide, carbocyclic nucleotide, phosphorodithioate linkage, inverted nucleotide or inverted abasic moiety (2'-3' or 3'-3'), phosphorodithioate monophosphate, and methylphosphonate moiety. The phosphorothioate or phosphorodithioate linkage(s), when part of a cap structure, are generally positioned between the two terminal nucleotides on the 5' end and the two terminal nucleotides on the 3' end.

In certain embodiments, the oligonucleotide has at least one terminal phosphorothioate monophosphate. The phosphorothioate monophosphate may support a higher potency by inhibiting the action of exonucleases. The phosphorothioate monophosphate may be at the 5' and/or 3' end of the oligonucleotide. A phosphorothioate monophosphate is defined by the following structures, where B is base, and R is a 2' modification as described above:

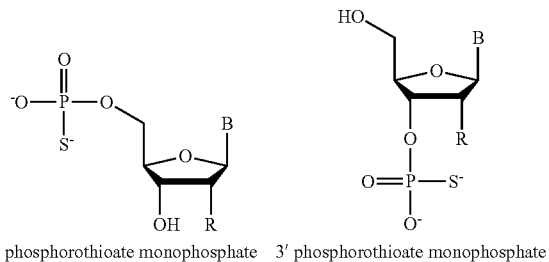

5' phosphorothioate monophosphate 3' phosphorothioate monophosphate

Where the cap structure can support the chemistry of a locked nucleotide, the cap structure may incorporate a LNA as described herein.

Phosphorothioate linkages may be present in some embodiments, such as between the last two nucleotides on the 5' and the 3' end (e.g., as part of a cap structure), or as alternating with phosphodiester bonds. In these or other embodiments, the oligonucleotide may contain at least one terminal abasic residue at either or both the 5' and 3' ends. An abasic moiety does not contain a commonly recognized purine or pyrimidine nucleotide base, such as adenosine, guanine, cytosine, uracil or thymine. Thus, such abasic moieties lack a nucleotide base or have other non-nucleotide base chemical groups at the 1' position. For example, the abasic nucleotide may be a reverse abasic nucleotide, e.g., where a reverse abasic phosphoramidite is coupled via a 5' amidite (instead of 3' amidite) resulting in a 5'-5' phosphate bond. The structure of a reverse abasic nucleoside for the 5' and the 3' end of a polynucleotide is shown below.

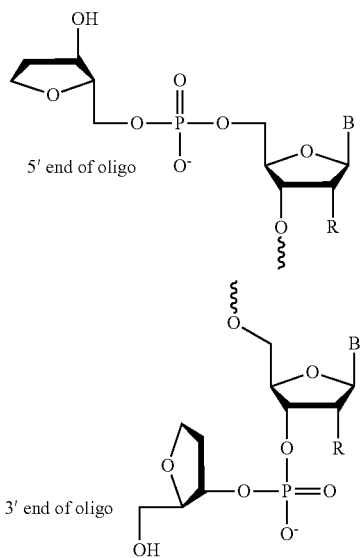

5' end of oligo

3' end of oligo

The oligonucleotide may contain one or more phosphorothioate linkages. Phosphorothioate linkages have been used to render oligonucleotides more resistant to nuclease cleavage. For example, the polynucleotide may be partially phosphorothioate-linked, for example, phosphorothioate linkages may alternate with phophodiester linkages. In certain embodiments, however, the oligonucleotide is fully phosphorothioate-linked. In other embodiments, the oligonucleotide has from one to five or one to three phosphate linkages.

In some embodiments, the nucleotide has one or more carboxamido-modified bases as described in WO 2012/061810, which is hereby incorporated by reference, including with respect to all exemplary pyrimidine carboxamido modifications disclosed therein with heterocyclic substituents.

The synthesis of oligonucleotides, including modified polynucleotides, by solid phase synthesis is well known and is reviewed in *New Chemical Methods for Synthesizing Polynucleotides*. Caruthers M H, Beaucage S L, Efcavitch J W, Fisher E F, Matteucci M D, Stabinsky Y. Nucleic Acids Symp. Ser. 1980; (7):215-23.

The oligonucleotide may be incorporated within a variety of macromolecular assemblies or compositions. Such complexes for delivery may include a variety of liposomes, nanoparticles, and micelles, formulated for delivery to a patient. The complexes may include one or more fusogenic or lipophilic molecules to initiate cellular membrane penetration. Such molecules are described, for example, in U.S. Pat. No. 7,404,969 and U.S. Pat. No. 7,202,227, which are hereby incorporated by reference in their entireties. Alternatively, the oligonucelotide may further comprise a pendent lipophilic group to aid cellular delivery, such as fatty acids and those described in WO 2010/129672, which is hereby incorporated by reference in its entirety. In some embodiments, the oligonucleotide may further comprise a pendent hydrophilic group to target the oligonucleotide to particular tissues. For instance, in one embodiment, the oligonucleotide may be conjugated to a sugar moiety, such as mannose-6-phosphate or an amino sugar, such as N-acetyl glucosamine.

The oligonucleotides of the invention may be formulated as a variety of pharmaceutical compositions. Pharmaceutical compositions will be prepared in a form appropriate for the intended application. Generally, this will entail preparing compositions that are essentially free of pyrogens, as well as other impurities that could be harmful to humans or animals. Exemplary delivery/formulation systems include colloidal dispersion systems, macromolecule complexes, nanocapsules, nanoparticles, microspheres, beads, and lipid-based systems including oil-in-water emulsions, micelles, mixed micelles, and liposomes. Commercially available fat emulsions that are suitable for delivering the nucleic acids of the invention to cardiac and skeletal muscle tissues include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO03/093449, all of which are hereby incorporated by reference in their entireties.

The compositions or formulations may employ a plurality of therapeutic oligonucleotides, including at least one described herein. For example, the composition or formulation may employ at least 2, 3, 4, or 5 miRNA inhibitors described herein. In another embodiment, an oligonucleotide of the present invention may be used in combination with other therapeutic modalities. Combinations may also be achieved by contacting the cell with more than one distinct compositions or formulations, at the same time. Alternatively, combinations may be administered sequentially.

In some embodiments, the oligonucleotide is formulated for conventional subcutaneous or intravenous administration, for example, by formulating with appropriate aqueous diluent, including sterile water and normal saline.

The pharmaceutical compositions and formulations may employ appropriate salts and buffers to render deliver vehicles stable and allow for uptake by target cells. Aqueous compositions of the present invention comprise an effective amount of the delivery vehicle comprising the inhibitor oligonucleotide (e.g. liposomes, nanoparticles, or other complexes), dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" may include one or more solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Supplementary active ingredients also can be incorporated into the compositions.

Administration or delivery of the pharmaceutical compositions according to the present invention may be via any route so long as the target tissue is available via that route. For example, administration may be topical or by intradermal, subcutaneous, intramuscular, intraperitoneal, intraarterial, intracoronary, intrathecal, or intravenous injection, or by direct injection into target tissue (e.g., cardiac tissue). The stability and/or potency of the oligonucleotides disclosed herein allows for convenient routes of administration, including subcutaneous, intradermal, intravenous, and intramuscular. Pharmaceutical compositions comprising an oligonucleotide described herein may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. Nos. 6,416,510; 6,716,196; and 6,953,466; PCT Publication Nos. WO 2005/082440 and WO 2006/089340; and U.S. Patent Publication Nos. 2007/0203445, 2006/0148742, and 2007/0060907, which are all hereby incorporated by reference in their entireties.

The compositions or formulations may also be administered parenterally or intraperitoneally. By way of illustration, solutions of the conjugates as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the conjugates in an appropriate amount into a solvent along with any other ingredients (for example as enumerated above) as desired. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

Upon formulation, solutions are preferably administered in a manner compatible with the dosage formulation and in such amount as is therapeutically effective. The formulations may easily be administered in a variety of dosage forms such as injectable solutions, drag release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The present invention provides a method for delivering oligonucleotides to a cell (e.g., as part of a composition or formulation described herein), and methods for treating, ameliorating, or preventing the progression of a condition in a subject. As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In other embodiments, the subject is a human.

The oligonucleotide or pharmaceutical composition may be contacted in vitro or in vivo with a target cell (e.g., a mammalian cell). The cell may be a kidney, liver, vascular, or heart cell.

The method generally comprises administering the oligonucleotide or composition comprising the same to a subject or cell. The oligonucleotide, as described herein, can be mRNA or miRNA inhibitor. In some embodiments, the miRNA inhibitor is not a miR-208a inhibitor, miR-208b inhibitor, or miR-499 inhibitor. Thus, the patient may have a condition associated with, mediated by, or resulting from, expression or dysregulation of a mRNA or miRNA. Such conditions include, but are not limited to, cardiovascular conditions, such as cardiac hypertrophy, myocardial infarction, heart failure (e.g., congestive heart failure), myocardial ischemia, ischemia-reperfusion injury, vascular damage, coronary artery disease, peripheral artery disease, vulnerable plaque, restenosis, or pathologic cardiac fibrosis. Other conditions may include metabolic conditions, renal conditions (e.g., renal ischemia), hepatic conditions, or pulmonary conditions. Thus, the invention provides a use of the modified oligonucleotides and compositions of the present invention for treating such conditions, and for the preparation of medicaments for such treatments.

In certain embodiments, the subject (e.g., human patient) has one or more risk factors for a condition, such as, but not limited to, long standing uncontrolled hypertension, uncorrected valvular disease, chronic angina, recent myocardial infarction, congestive heart failure, congenital predisposition to heart disease and pathological hypertrophy. Alternatively or in addition, the patient may have been diagnosed as having a genetic predisposition to, for example, cardiac hypertrophy, or may have a familial history of, for example, cardiac hypertrophy.

In this aspect, the present invention may provide for an improved exercise tolerance, reduced hospitalization, better quality of life, decreased morbidity, and/or decreased mortality in a patient with heart failure or cardiac hypertrophy.

In certain embodiments, the activity of the miRNA in a tissue of interest, such as cardiac tissue, or as determined in serum, is reduced or inhibited.

In various embodiments, the pharmaceutical composition is administered by parenteral administration or by direct injection into heart tissue. The parenteral administration may be intravenous, subcutaneous, or intramuscular. In some embodiments, the composition is administered by oral, transdermal, sustained release, controlled release, delayed release, suppository, catheter, or sublingual administration. In certain embodiments, the oligonucleotide is administered at a dose of about 25 mg/kg or less, or a dose of about 10 mg/kg or less, or a dose of about 5 mg/kg or less. In these embodiments, the oligonucleotide or composition may be administered by intramuscular or subcutaneous injection, or intravenously.

In some embodiments, the methods further comprise scavenging or clearing the miRNA inhibitors following treatment. For example, a polynucleotide having a nucleotide sequence that is complementary to the inhibitor (e.g., a polynucleotide comprising a miRNA sequence) may be administered after therapy to attenuate or stop the function of the inhibitor.

The present invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

All publications and patents and patent applications mentioned in this specification are herein incorporated by reference to the same extent as if each individual publication, patent or patent application was specifically and individually indicated to be incorporated by reference.

EXAMPLES

Example 1

In Vivo Efficacy of AntimiR-208a

To determine whether the location of the LNA base affects in vivo efficacy of microRNA inhibitors (antimiRs) of identical length and LNA percentage, several antimiRs with different LNA modification patterns were designed and tested for efficacy in inhibiting miRNA function in vivo.

Sixteen antimiRs against miR-208a (FIG. 1A) with varying Tm measurements were designed, as depicted in Table 3 below:

TABLE 3

| Molecule # | Alias | Sequence | Length | LNA/DNA | Predicted Tm |
|---|---|---|---|---|---|
| M-10101 | 208a_LNA_DNA_16_PS | lCs; dTs; dTs; dTs; lTs; lTs; dGs; lCs; dTs; lCs; lGs; dTs; lCs; dTs; lTs; lA (SEQ ID NO: 76) | 16 | 9/7 | 81 |
| M-10679 | 208a LNA C_T_DNA_16_1 | lCs; dTs; lTs; dTs; lTs; lTs; dGs; lCs; dTs; lCs; dGs; lTs; dCs; lTs; lTs; dA (SEQ ID NO: 77) | 16 | 9/7 | 93 |
| M-10680 | 208a_LNA_opt_1 | lCs; dTs; lTs; lTs; lTs; lTs; dGs; lCs; dTs; lCs; dGs; dTs; lCs; dTs; dTs; lA (SEQ ID NO: 78) | 16 | 9/7 | 90 |

TABLE 3-continued

| Molecule # | Alias | Sequence | Length | LNA/DNA | Predicted Tm |
|---|---|---|---|---|---|
| M-10681 | 208a_LNA_opt_2 | lCs; dTs; lTs; lTs; dTs; lTs; dGs; lCs; lTs; lCs; dGs; dTs; lCs; dTs; lTs; dA (SEQ ID NO: 79) | 16 | 9/7 | 93 |
| M-10682 | 208a_LNA_opt_3 | lCs; dTs; lTs; dTs; lTs; dTs; lGs; dCs; lTs; dCs; lGs; dTs; lCs; dTs; lTs; lA (SEQ ID NO: 80) | 16 | 9/7 | 86 |
| M-10683 | 208a_LNA_opt_4 | lCs; dTs; dTs; lTs; lTs; dTs; lGs; dCs; lTs; lCs; dGs; lTs; dCs; lTs; dTs; lA (SEQ ID NO: 81) | 16 | 9/7 | 92 |
| M-10673 | 208a_LNA_opt_5 | lCs; dTs; lTs; lTs; lTs; dTs; dGs; lCs; dTs; lCs; dGs; dTs; lCs; dTs; lTs; dA (SEQ ID NO: 82) | 16 | 9/7 | 93 |
| M-11184 | 208a_10626 | lCs; dTs; lTs; lTs; dTs; dTs; lGs; lCs; dTs; lCs; dGs; lTs; dCs; lTs; dTs; lA (SEQ ID NO: 83) | 16 | 9/7 | 83 |
| M-11293 | 208a_scr2_1 | lCs; dTs; dTs; dTs; lTs; lTs; dGs; dCs; lTs; lCs; lGs; dTs; lCs; dTs; lTs; lA (SEQ ID NO: 84) | 16 | 9/7 | 86 |
| M-11294 | 208a_scr2_2 | lCs; lTs; dTs; dTs; dTs; lTs; dGs; lCs; lTs; lCs; lGs; dTs; lCs; dTs; lTs; lA (SEQ ID NO: 85) | 16 | 9/7 | 77 |
| M-11295 | 208a_scr2_3 | lCs; lTs; dTs; dTs; dTs; lTs; lGs; dCs; dTs; lCs; lGs; lTs; dCs; lTs; dTs; lA (SEQ ID NO: 86) | 16 | 9/7 | 76 |
| M-11296 | 208a_scr2_4 | lCs; dTs; dTs; dTs; lTs; lTs; dGs; lCs; lTs; lCs; lGs; dTs; lCs; lTs; dTs; lA (SEQ ID NO: 87) | 16 | 9/7 | 80 |
| M-11297 | 208a_scr2_5 | lCs; lTs; dTs; dTs; lTs; dTs; dGs; lCs; lTs; lCs; dGs; lTs; dCs; lTs; dTs; lA (SEQ ID NO: 88) | 16 | 9/7 | 87 |
| M-11298 | 208a_scr2_6 | lCs; dTs; lTs; dTs; lTs; lTs; lGs; lCs; lTs; lCs; dGs; lTs; dCs; lTs; dTs; lA (SEQ ID NO: 89) | 16 | 9/7 | 83 |
| M-11299 | 208a_scr2_7 | lCs; dTs; dTs; lTs; lTs; dTs; lGs; lCs; dTs; lCs; dGs; lTs; dCs; lTs; dTs; lA (SEQ ID NO: 90) | 16 | 9/7 | 83 |
| M-11300 | 208a_scr2_8 | lCs; lTs; dTs; dTs; lTs; dTs; lGs; dCs; lTs; lCs; dGs; lTs; dCs; lTs; dTs; lA (SEQ ID NO: 91) | 16 | 9/7 | 88 |

TABLE 4

| Description of Notations | |
|---|---|
| deoxy A | dA |
| deoxy G | dG |
| deoxy C | dC |
| deoxy T | dT |
| lna A | lA |
| lnaG | lG |
| lna C | lC |
| lna T | lT |
| deoxy A P = S | dAs |
| deoxy G P = S | dGs |
| deoxy C P = S | dCs |
| deoxy T P = S | dTs |
| lna A P = S | lAs |
| lnaG P = S | lGs |
| lna C P = S | lCs |
| lna T P = S | lTs |

Figure 1C:
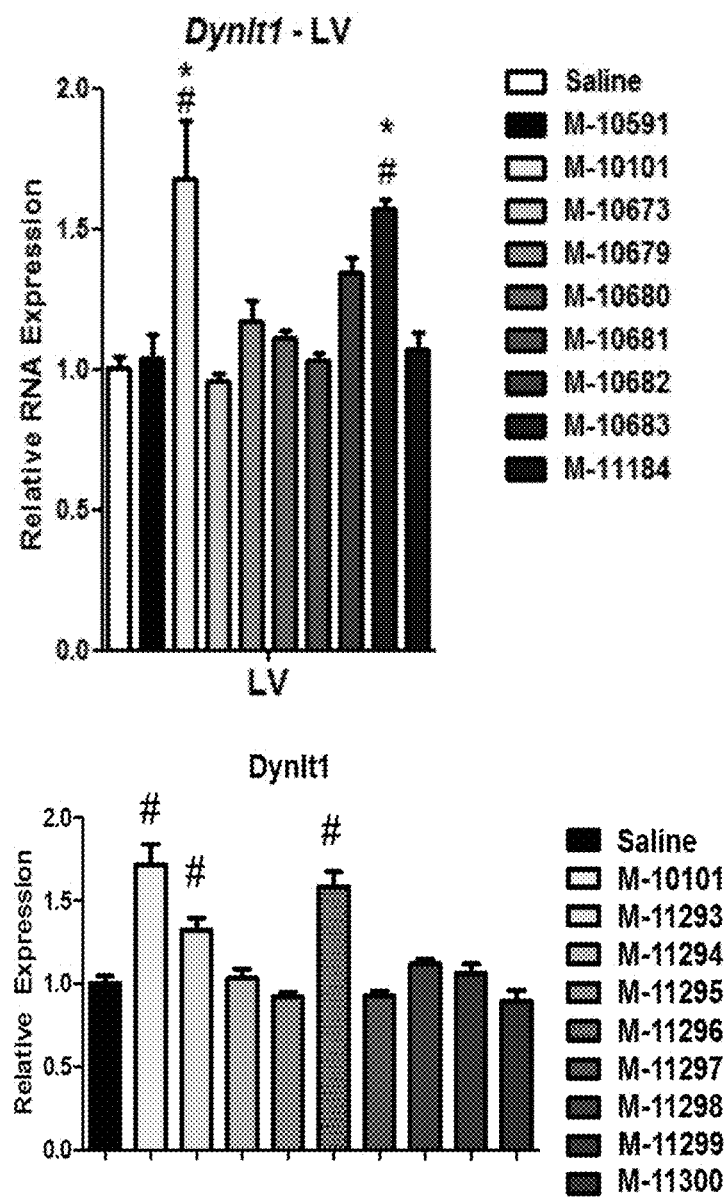

These antimiRs were dorsally injected into 6-8 week old Sprague Dawley rats subcutaneously at a dose of 25 mg/kg (n=4 per group). Injection volume was 1.0 mL. A control oligonucleotide with similar LNA and DNA percentage (9/7) was also used as a chemistry control. This molecule number is M-10591 and was designed to target a *C. elegans*—specific miRNA. Four days after a single dose, these rats were sacrificed and plasma was collected for liver and kidney toxicology parameters. Additionally, heart, liver, and kidney were collected for molecular analysis including miRNA inhibition, target de-repression, and antimiR-distribution quantification. RNA was isolated from cardiac tissue and real-time PCR was performed. All antimiRs designed against miR-208a showed significant inhibition of miR-208a suggesting all antimiRs were delivered to cardiac tissue (FIG. 1B). To determine if miR-208a inhibition correlated to in vivo efficacy, miR-208a targets were assessed for de-repression by performing real-time PGR for the miR-208a target, Dynlt1. Surprisingly, only four of the sixteen antimiRs tested showed significant de-repression of Dynlt1 (FIG. 1C).

Figure 1D:
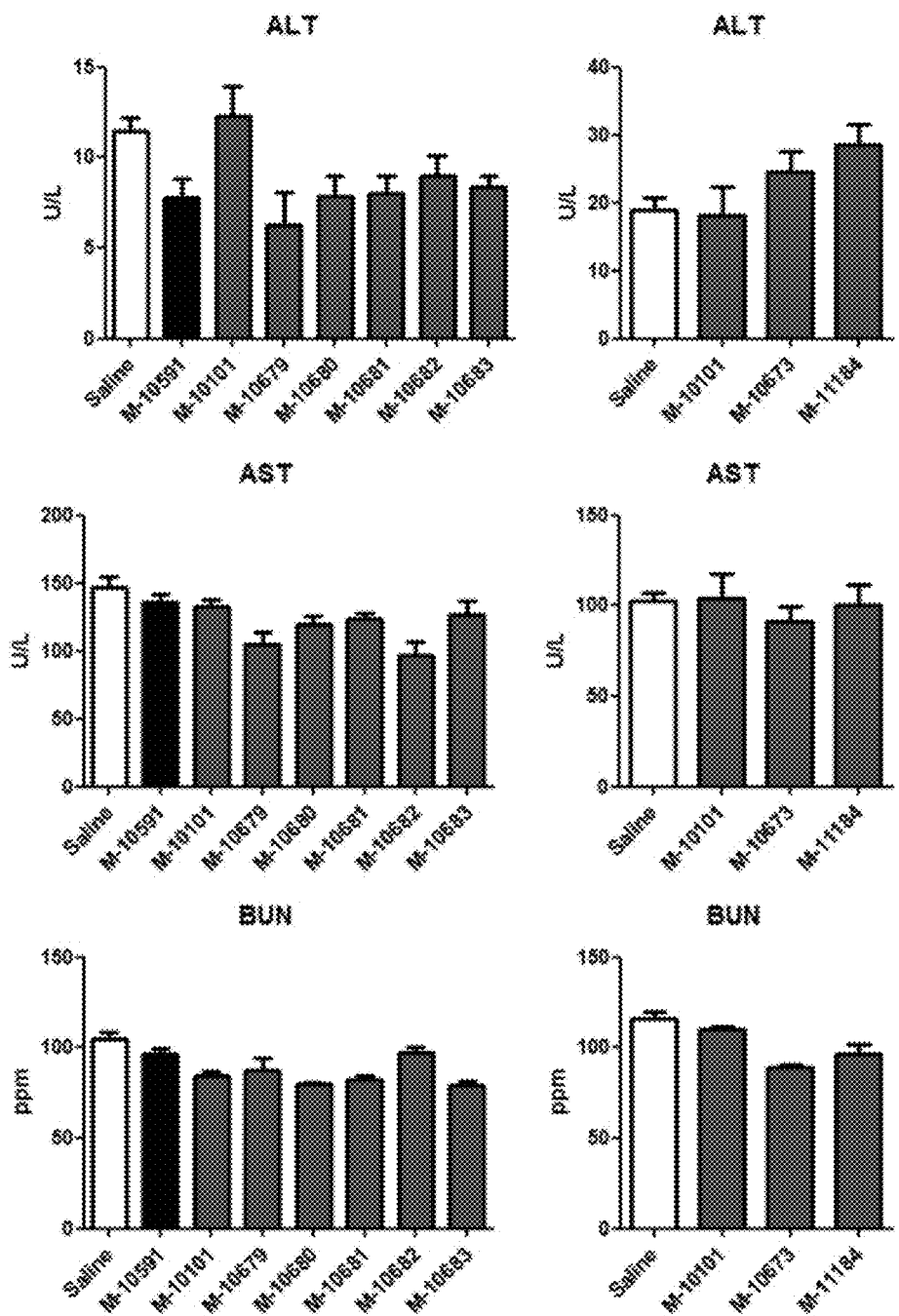
Figure 1D:
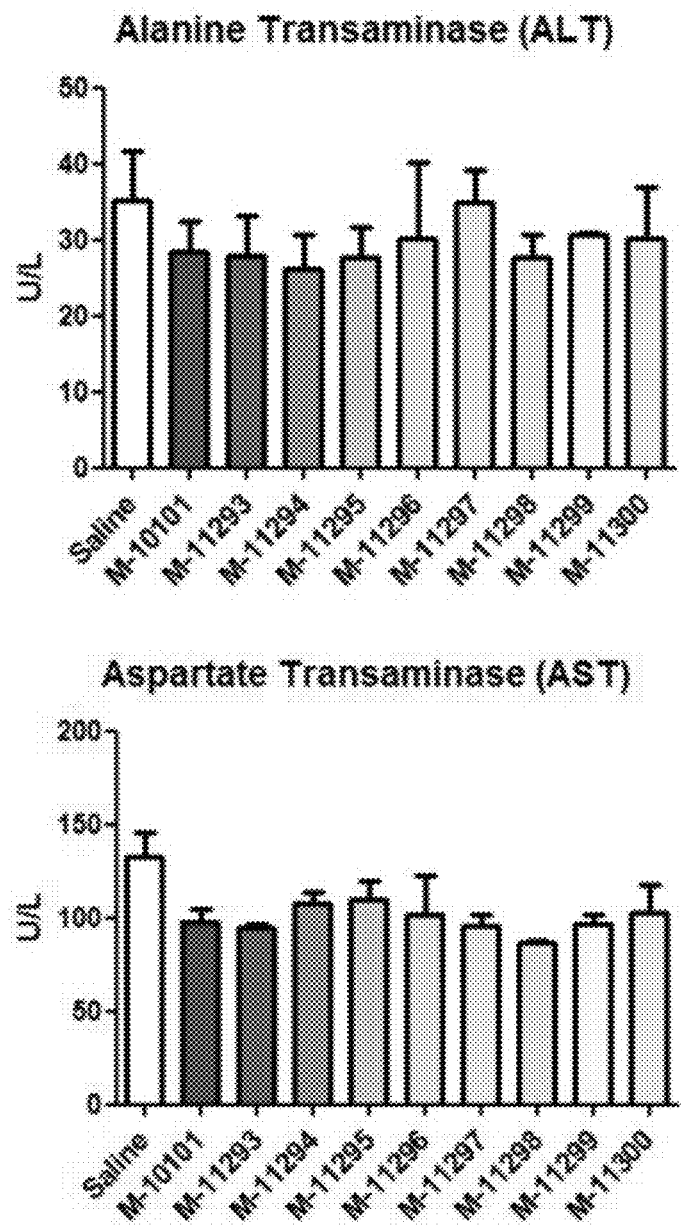

To determine if treatment with any of these antimiRs resulted in elevated liver and/or kidney toxicology parameters, ELISAs for ALT, AST, and BUN were performed to assess liver and kidney function. No antimiR-treated group showed any elevation in either liver or kidney toxicology parameters (FIG. 1D).

Figure 1E:
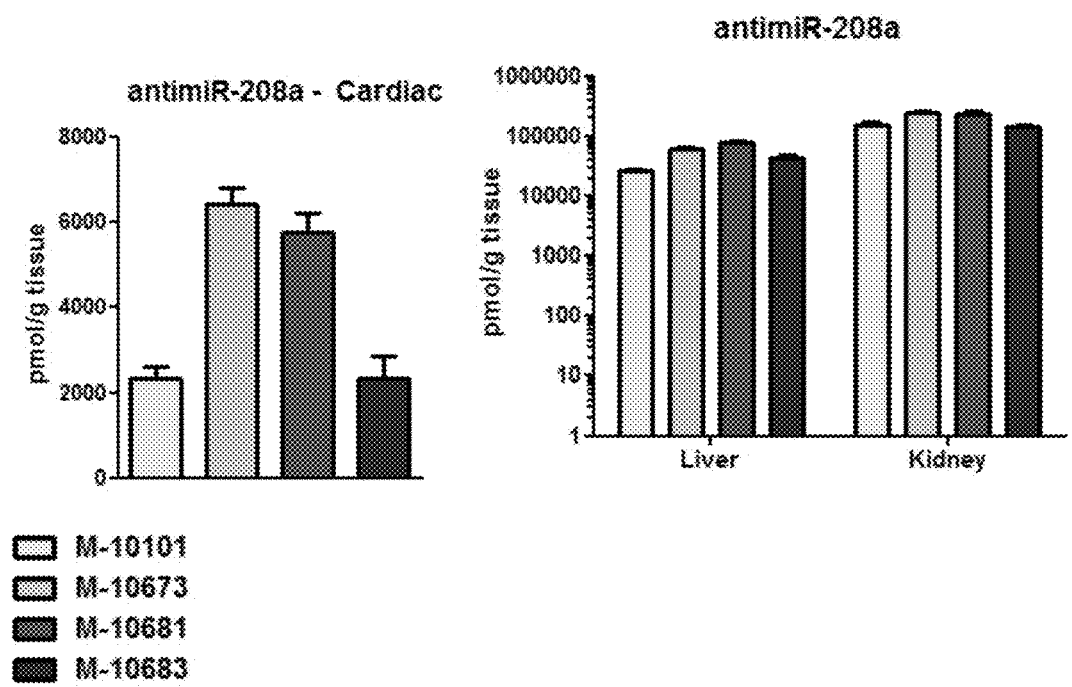

To determine if the difference in efficacy between compounds is due to better cardiac distribution for the efficacious molecules, antimiR distribution to the heart, liver, and kidney for 2 antimiRs that showed efficacy (M-10101 and M-10683) and 2 antimiRs that did not show efficacy (M-10673 and M-10681) were assessed. ELISA-based distribution analyses showed no better cardiac presence for the efficacious compounds compared to the non-efficacious compounds. In fact, the non-efficacious compounds appeared to show better distribution to all tissues. (FIG. 1E).

These data suggest different LNA and DNA placement within the antimiR, results in significantly different antimiR efficacy as it pertains to the heart, with the LNA/DNA "motif" of M-10101 sequence appearing to be the best compound for cardiac efficacy.

Example 2

In Vivo Efficacy of AntimiR-208b

To test if the efficacious LNA/DNA motif of M-10101 remains efficacious for additional miRNAs, a subset of these for other miRNAs, including miR-208b, miR-29, miR-378, miR-199a, and miR-92a was tested. All experimental designs were the same as performed for miR-208a as described in Example 1.

Nine antimiRs against miR-208b with LNA and DNA placements similar to those found for the miR-208a screen were synthesized (FIG. 2A), with varying Tm measurements was designed, as depicted in Table 5 below (description of notations is as described in Table 4):

TABLE 5

| Molecule # | Alias | Sequence | Length | LNA/DNA | Predicted Tm |
|---|---|---|---|---|---|
| M-10707 | 208b_10101 | lCs; dCs; dTs; dTs; lTs; lTs; dGs; lTs; dTs; lCs; lGs; dTs; lCs; dTs; lTs; lA (SEQ ID NO: 92) | 16 | 9/7 | 82 |
| M-11283 | 208b_10679 | lCs; dCs; lTs; dTs; lTs; lTs; dGs; lTs; dTs; lCs; dGs; lTs; dCs; lTs; lTs; dA (SEQ ID NO: 93) | 16 | 9/7 | 91 |
| M-11284 | 208b_10680 | lCs; dCs; lTs; lTs; lTs; lTs; dGs; lTs; dTs; lCs; dGs; dTs; lCs; dTs; dTs; lA (SEQ ID NO: 94) | 16 | 9/7 | 89 |
| M-11285 | 208b_10681 | lCs; dCs; lTs; lTs; dTs; lTs; dGs; lTs; lTs; lCs; dGs; dTs; lCs; dTs; lTs; dA (SEQ ID NO: 95) | 16 | 9/7 | 94 |
| M-11286 | 208b_10682 | lCs; dCs; lTs; dTs; lTs; dTs; lGs; dTs; lTs; dCs; lGs; dTs; lCs; dTs; lTs; lA (SEQ ID NO: 96) | 16 | 9/7 | 86 |
| M-11287 | 208b_10683 | lCs; dCs; dTs; lTs; lTs; dTs; lGs; dTs; lTs; lCs; dGs; lTs; dCs; dTs; lTs; lA (SEQ ID NO: 97) | 16 | 9/7 | 93 |
| M-11288 | 208b_10673 | lCs; dCs; lTs; lTs; lTs; lTs; dGs; lTs; dTs; lCs; dGs; dTs; lCs; dTs; lTs; dA (SEQ ID NO: 98) | 16 | 9/7 | 91 |
| M-11289 | 208b_10626 | lCs; dCs; lTs; lTs; dTs; dTs; lGs; lTs; dTs; lCs; dGs; lTs; dCs; dTs; lTs; lA (SEQ ID NO: 99) | 16 | 9/7 | 89 |
| M-11290 | 208b_LNA_opt6 | lCs; lCs; dTs; dTs; lTs; dTs; lGs; lTs; dTs; lCs; dGs; lTs; dCs; lTs; dTs; lA (SEQ ID NO: 100) | 16 | 9/7 | 92 |

Figures 2A, 2B:
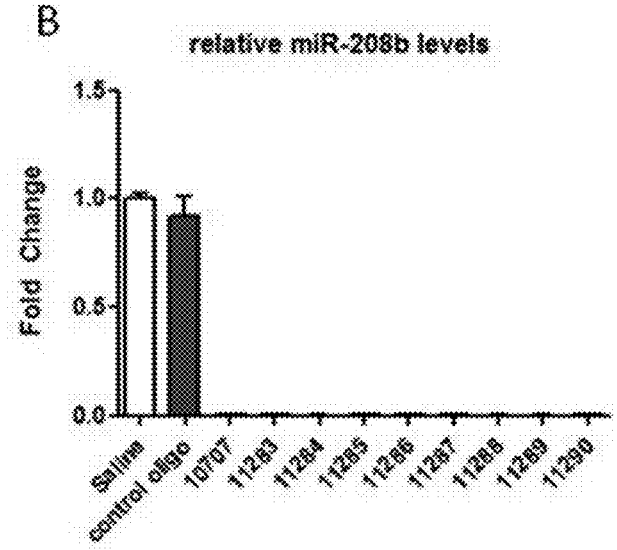
FIG. 2. (A) Location of LNA and DNA bases for 9 antimiRs designed to target miR-208b (SEQ ID NOs: 92-100). LNA bases are represented by a capital letter. DNA bases are represented by a lower case letter. (B) MiR-208b inhibition by antimiR-208b compounds. All antimiR compounds showed significant miR-208b inhibition in the left ventricle. (C) Real-time PCR from cardiac tissue of antimiR-208b treated rats showed differing target de-repression in vivo using Dynlt1 as a primary readout for efficacy and target de-repression. *$p<0.05$ vs. Saline FIG. 3. Silencing. (A) Location of LNA and DNA bases for 7 antimiRs designed to target miR-378 (SEQ ID NOs: 101-107). LNA bases are represented by a capital letter. DNA bases are represented by a lower case letter. (B) MiR-378 inhibition by antimiR-378 compounds. All antimiR compounds showed significant miR-378 inhibition in the left ventricle. (C) Real-time PCR from cardiac tissue of antimiR-378 treated rats showed differing target de-repression in vivo using Gfpt2 as a primary readout for efficacy and target de-repression. #p<0.05 vs. Saline FIG. 4, (A) Location of LNA and DNA bases for 7 anti-miRs designed to target miR-29 (SEQ ID NOs: 108-114). LNA bases are represented by a capital letter. DNA bases are represented by a lower case letter. (B) MiR-29 family inhibition by antimiR-29 compounds in heart (top panel), liver (middle panel), and kidney (bottom panel). All antimiR compounds showed significant miR-29 family inhibition in heart, liver, and kidney, (C) Real-time PCR from heart (top panel), liver (middle panel), and kidney (bottom panel) of antimiR-29 treated rats showed differing target de-repression in vivo using Dnmt3b and Mcl1 as a primary readout for efficacy and target de-repression. *p<0.05 vs. Saline; #p<0.05 vs. Control oligonucleotide M-10591. (D) Quantification of antimiR compounds from heart and liver four days after a single 25 mg/kg subcutaneous dose. Distribution to the heart is much lower than liver. More efficacious compounds are not more robustly distributed to the heart compared to less efficacious compounds.

These antimiRs were dorsally injected into 6-8 week old Sprague Dawley rats subcutaneously at a dose of 25 mg kg (n=4 per group). Injection volume was 1.0 ml. A control oligonucleotide with similar LNA and DNA percentage (9/7) was also used as a chemistry control. This molecule number is M-10591 and was designed to target a *C. elegans*—specific miRNA. Four days after a single dose, these rats were sacrificed and the heart was collected for molecular analysis including miRNA inhibition and target de-repression. RNA was isolated from cardiac tissue and real-time PGR was performed. All antimiRs designed against miR-208b showed significant inhibition of miR-208b suggesting all antimiRs were delivered to cardiac tissue (FIG. 2B). To determine if miR-208b inhibition correlated to in vivo efficacy, the miR-208b target, Dynlt1, was assessed for de-repression by performing real-time PGR. Surprisingly, only M-10707 showed significant de-repression of Dynlt1 (FIG. 2C), which is the same LNA/DNA motif that showed the best efficacy for miR-208a. (FIG. 1C).

These data suggest the LNA/DNA motif of M-10101 and M-10707 (which is the same) confers cardiac efficacy in vivo.

Example 3

In Vivo Efficacy of AntimiR-378

To determine if motif M-10101 extends beyond the miR-208 family, 7 antimiRs against miR-378 with LNA and DNA placements similar to those found for the miR-208a screen (FIG. 3A), with varying Tm measurements as depicted in Table 6 below (description of notations is as described in Table 4), were designed and synthesized:

TABLE 6

| Molecule # | Alias | Sequence | Length | LNA/DNA | Predicted Tm |
|---|---|---|---|---|---|
| M-11192 | 378_10101 | lCs; dTs; dGs; dAs; lCs; lTs; dCs; lCs; dAs; lAs; lGs; dTs; lCs; dCs; lAs; lGs (SEQ ID NO: 101) | 16 | 9/7 | 86 |
| M-11193 | 378_10680 | lCs; dTs; lGs; lAs; lCs; lTs; dCs; lCs; dAs; lAs; dGs; dTs; lCs; dCs; dAs; lGs (SEQ ID NO: 102) | 16 | 9/7 | 89 |
| M-11194 | 378_10681 | lCs; dTs; lGs; lAs; dCs; lTs; dCs; lCs; lAs; lAs; dGs; dTs; dCs; lAs; dGs (SEQ ID NO: 103) | 16 | 9/7 | 89 |
| M-11195 | 378_10682 | lCs; dTs; lGs; dAs; lCs; dTs; lCs; dCs; lAs; dAs; lGs; dTs; lCs; dCs; lAs; lGs (SEQ ID NO: 104) | 16 | 9/7 | 86 |
| M-11196 | 378_10683 | lCs; dTs; dGs; lAs; lCs; dTs; lCs; dCs; lAs; lAs; dGs; lTs; dCs; lCs; dAs; lGs (SEQ ID NO: 105) | 16 | 9/7 | 91 |
| M-11197 | 378_10673 | lCs; dTs; lGs; lAs; lCs; lTs; dCs; lCs; dAs; lAs; dGs; dTs; lCs; dCs; lAs; dGs (SEQ ID NO: 106) | 16 | 9/7 | 95 |
| M-11198 | 378_10626 | lCs; dTs; lGs; lAs; dCs; dTs; lCs; lCs; dAs; lAs; dGs; lTs; lCs; dCs; dAs; lGs (SEQ ID NO: 107) | 16 | 9/7 | 95 |

Figure 2C:
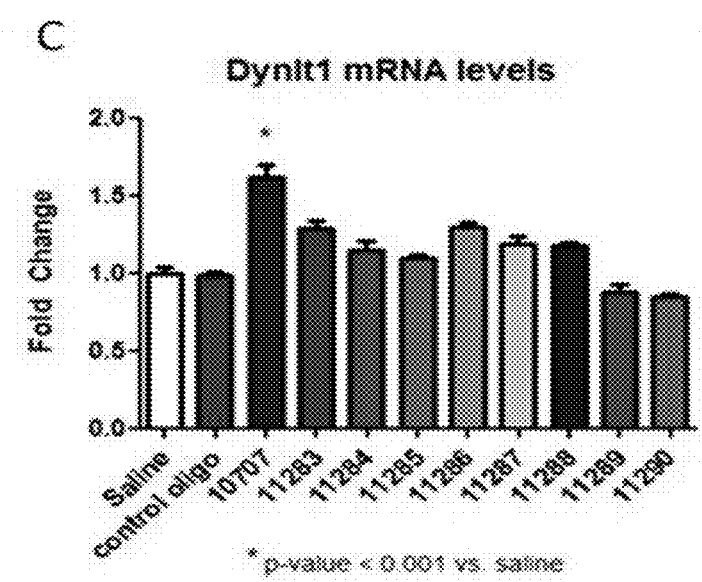
Figures 3A, 3B:
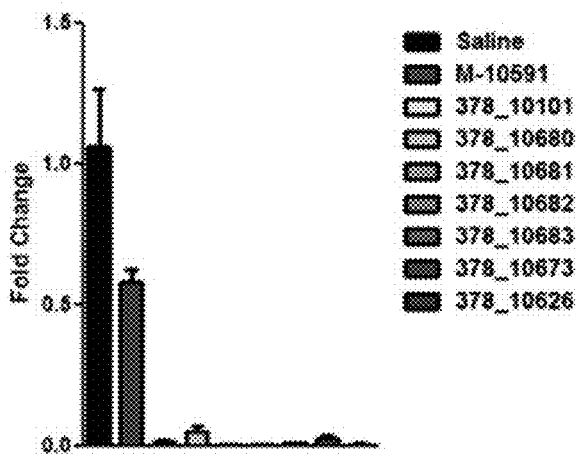

These antimiRs were dorsally injected into 6-8 week old Sprague Dawley rats subcutaneously at a dose of 25 mg/kg (n=4 per group). Injection volume was 1.0 ml. A control oligonucleotide with similar LNA, and DNA percentage (9/7) was also used as a chemistry control. This molecule number is M-10591 and was designed to target a *C. elegans*—specific miRNA. Four days after a single dose, these rats were sacrificed and the heart was collected for molecular analysis including miRNA inhibition and target de-repression. RNA was isolated from cardiac tissue and real-time PCR was performed. All antimiRs designed against miR-378 showed significant inhibition of miR-378 suggesting all antimiRs were delivered to cardiac tissue (FIG. 3B). To determine if miR-378 inhibition correlated to in vivo efficacy, we assessed the miR-378 target, Gfpt2, for de-repression by performing real-time PCR. Surprisingly, only M-11192 showed significant de-repression of Gfpt2 (FIG. 3C), which is the same LNA/DNA motif that showed the best efficacy for miR-208a and miR-208b in the heart. (FIGS. 1C and 2C).

These data highly suggest the LNA/DNA motif of M-10101, M-10707, and M-11192 (which is the same) confers cardiac efficacy in vivo.

Example 4

In Vivo Efficacy of AntimiR-29

Figure 4B:
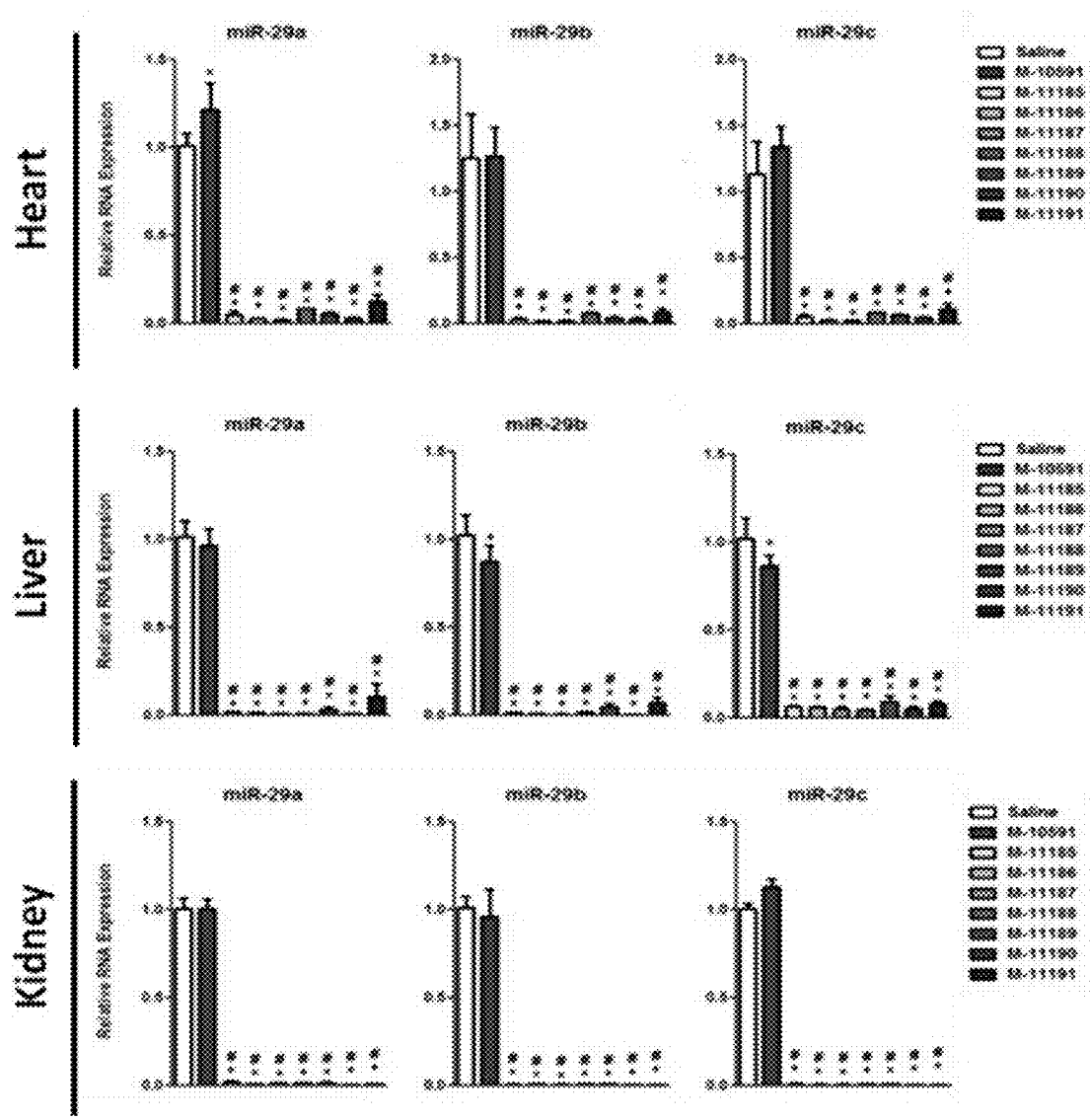

Seven antimiRs against miR-29b with LNA and DNA placements similar to those found for the miR-208a screen (FIG. 4A) were synthesized to determine if this motif confers efficacy in further miRNA families. The sequence and modification patterns of these antimiRs with their corresponding predicted Tm values are depicted in Table 7 below (description of notations is as described in Table 4):

molecular analysis including miRNA inhibition, target de-repression, and antimiR-distribution quantification, RNA was isolated from cardiac, hepatic, and renal tissue and real-time PCR was performed. All antimiRs designed against miR-29 showed significant inhibition of miR-29 family members in all tissues suggesting all antimiRs were delivered to these three tissues (FIG. 4B).

Figure 3C:
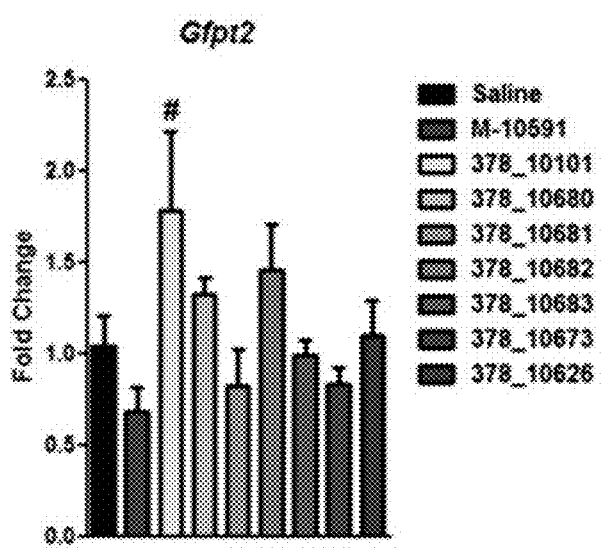
Figure 4C:
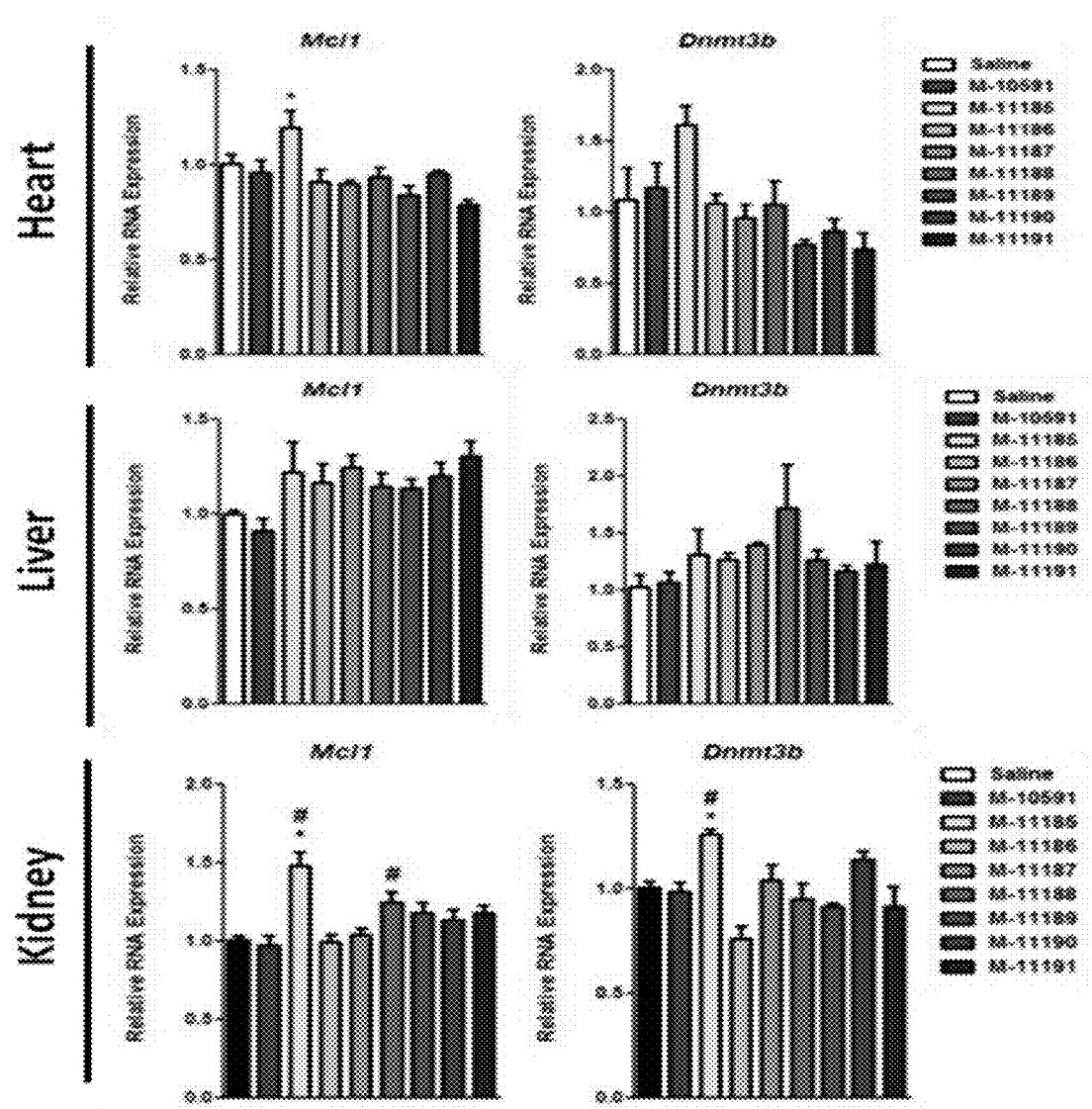

To determine if miR-29 family inhibition correlated with in vivo efficacy, the miR-29 targets, Mcl1 and Dnmt3b, were assess for de-repression by performing real-time PGR. Surprisingly, only M-11185 showed significant de-repression of Mcl1 in the heart and trending de-repression of Dnmt3b (FIG. 4C), which is the same LNA/DNA motif that showed the best efficacy for miR-208a, miR-208b, and miR-378 in the heart. (FIGS. 1C, 2C, and 3C). Surprisingly, all antimiR-29 compounds appeared to show de-repression of Mcl1 in the liver, furthering the notion that this motif confers cardiac efficacy while the other compounds are active in other tissues.

Figure 4D:
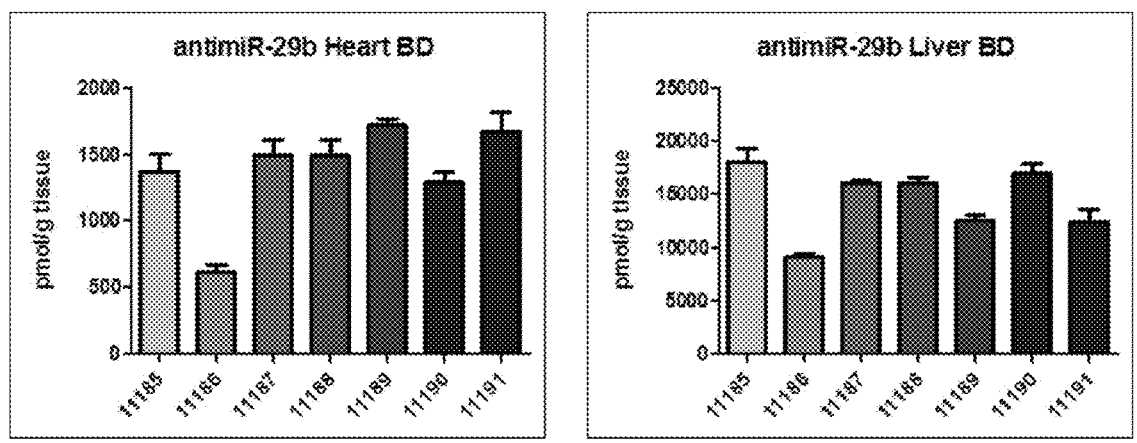

To determine if the difference in efficacy between compounds is due to better cardiac distribution for the efficacious molecules, we quantified antimiR distribution to the heart and liver for all antimiR-29 compounds. ELISA-based distribution analyses showed no better cardiac presence for the most efficacious compound (M-11185) compared to the less efficacious compounds. For hepatic tissue where efficacy was similar among compounds, distribution was similar as well (FIG. 4D).

Example 5

In Vivo Efficacy of AntimiR-199

Five antimiRs against miR-199a with LNA and DNA placements similar to those found for the miR-208a screen

TABLE 7

| Molecule # | Alias | Sequence | Length | LNA/DNA | Predicted Tm |
|---|---|---|---|---|---|
| 11185 | 29b_10101 | lGs; dAs; dTs; dTs; lTs; lCs; dAs; lAs; dAs; lTs; lGs; dGs; lTs; dGs; lCs; lTs (SEQ ID NO: 108) | 16 | 9/7 | 84 |
| 11186 | 29b_10680 | lGs; dAs; lTs; lTs; lTs; lCs; dAs; dAs; dAs; lTs; dGs; dGs; lTs; dGs; dCs; lTs (SEQ ID NO: 109) | 16 | 9/7 | 91 |
| 11187 | 29b_10681 | lGs; dAs; lTs; lTs; dTs; lCs; dAs; lAs; lAs; lTs; dGs; dGs; lTs; dGs; lCs; dTs (SEQ ID NO: 110) | 16 | 9/7 | 87 |
| 11188 | 29b_10682 | lGs; dAs; lTs; dTs; lTs; dCs; lAs; dAs; lAs; dTs; lGs; dGs; lTs; dGs; lCs; lTs (SEQ ID NO: 111) | 16 | 9/7 | 82 |
| 11189 | 29b_10683 | lGs; dAs; dTs; lTs; lTs; dCs; lAs; dAs; lAs; lTs; dGs; lGs; dTs; lGs; dCs; lTs (SEQ ID NO: 112) | 16 | 9/7 | 85 |
| 11190 | 29b_10673 | lGs; dAs; lTs; lTs; lTs; lCs; dAs; lAs; dTs; dGs; dGs; lTs; dGs; lCs; dTs (SEQ ID NO: 113) | 16 | 9/7 | 96 |
| 11191 | 29b_10626 | lGs; dAs; lTs; lTs; dTs; dCs; lAs; lAs; dAs; lTs; dGs; lGs; dTs; lGs; dCs; lTs (SEQ ID NO: 114) | 16 | 9/7 | 82 |

These antimiRs were dorsally injected into 6-8 week old Sprague Dawley rats subcutaneously at a dose of 25 mg/kg (n=4 per group). Injection volume was 1.0 mL. A control oligonucleotide with similar LNA and DNA percentage (9/7) was also used as a chemistry control. This molecule number is M-10591 and was designed to target a *C. elegans*—specific miRNA. Four days after a single dose, these rats were sacrificed and the heart, liver, and kidney were collected for (FIG. 5A) were synthesized to determine if this motif confers efficacy in further miRNA families. The sequence and modification patterns of these antimiRs with their corresponding predicted Tm values are depicted in Table 8 below (description of notations is as described in Table 4). The M-10518 compound contains the same LNA and DNA placements as M-10101 (antimiR-208a), M-10707 (antimiR-208b), M-11192 (antimiR-378), and M-11185 (antimiR-29).

TABLE 8

| Molecule # | Alias | Sequence | Length | LNA/DNA | Predicted Tm |
|---|---|---|---|---|---|
| 10518 | 199a_10101 | lGs; dTs; dAs; dGs; lTs; lCs; dTs; lGs; dAs; lAs; lCs; dAs; lCs; dTs; lGs; lGs (SEQ ID NO: 115) | 16 | 9/7 | 93 |
| 11390 | 199a_10293 | lGs; dTs; dAs; dGs; lTs; lCs; dTs; dGs; lAs; lAs; lCs; dAs; lCs; dTs; lGs; lGs (SEQ ID NO: 116) | 16 | 9/7 | 92 |
| 11391 | 199a_10294 | lGs; lTs; dAs; dGs; dTs; lCs; dTs; lGs; dAs; lAs; lCs; dAs; lCs; dTs; lGs; lGs (SEQ ID NO: 117) | 16 | 9/7 | 86 |
| 11392 | 199a_10296 | lGs; dTs; dAs; dGs; lTs; lCs; dTs; lGs; dAs; lAs; lCs; dAs; lCs; lTs; dGs; lGs (SEQ ID NO: 118) | 16 | 9/7 | 92 |
| 11393 | 199a_10683 | lGs; dTs; dAs; lGs; lTs; dCs; lTs; dGs; lAs; lAs; dCs; lAs; dCs; lTs; dGs; lGs (SEQ ID NO: 119) | 16 | 9/7 | 86 |

Figure 5B:
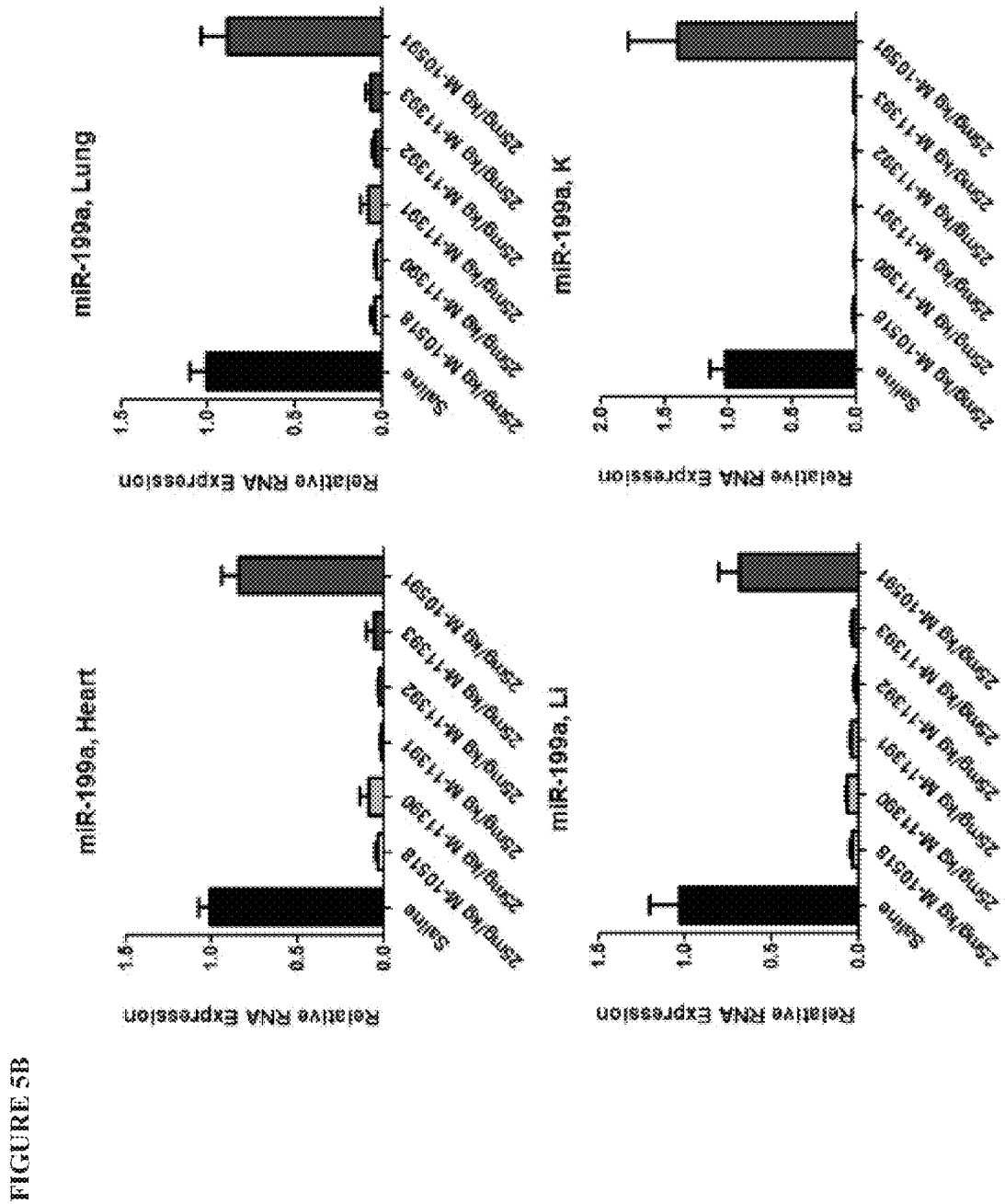
FIG. 5. (A) Location of LNA and DNA bases for 5 anti-miRs designed to target miR-199a (SEQ ID NOs: 115-119). LNA bases are represented by a capital letter. DNA bases are represented by a lower case letter. (B) MiR-199a inhibition by antimiR-199 compounds in heart, lung, liver (Li), and kidney (K). All antimiR compounds showed significant miR-199a inhibition in heart, lung, liver, and kidney. (C) Real-time PGR from heart, lung, liver (Li), and kidney (K) of antimiR-199-treated rats showed differing target de-repression in vivo using Ddr1 as a primary readout for efficacy and target de-repression. M-10518 consistently appeared to show target de-repression across multiple tissues. *p<0.05 vs. Saline.

These antimiRs were dorsally injected into 6-8 week old Sprague Dawley rats subcutaneously at a dose of 25 mg/kg (n=4 per group). Injection volume was 1.0 mL. A control oligo with similar LNA and DNA percentage (9/7) was also used as a chemistry control. This molecule number is M-10591 and was designed to target a *C. elegans*—specific miRNA. Four days after a single dose, these rats were sacrificed and plasma was collected for liver and kidney toxicology parameters. Additionally, heart, lung, liver, and kidney were collected for molecular analysis including miRNA inhibition and target de-repression. RNA was isolated from cardiac, pulmonary, hepatic, and renal tissue and real-time PCR was performed. All antimiRs designed against miR-199a showed significant inhibition of miR-199a in all tissues suggesting all antimiRs were delivered to these four tissues (FIG. 5B).

Figure 5C:
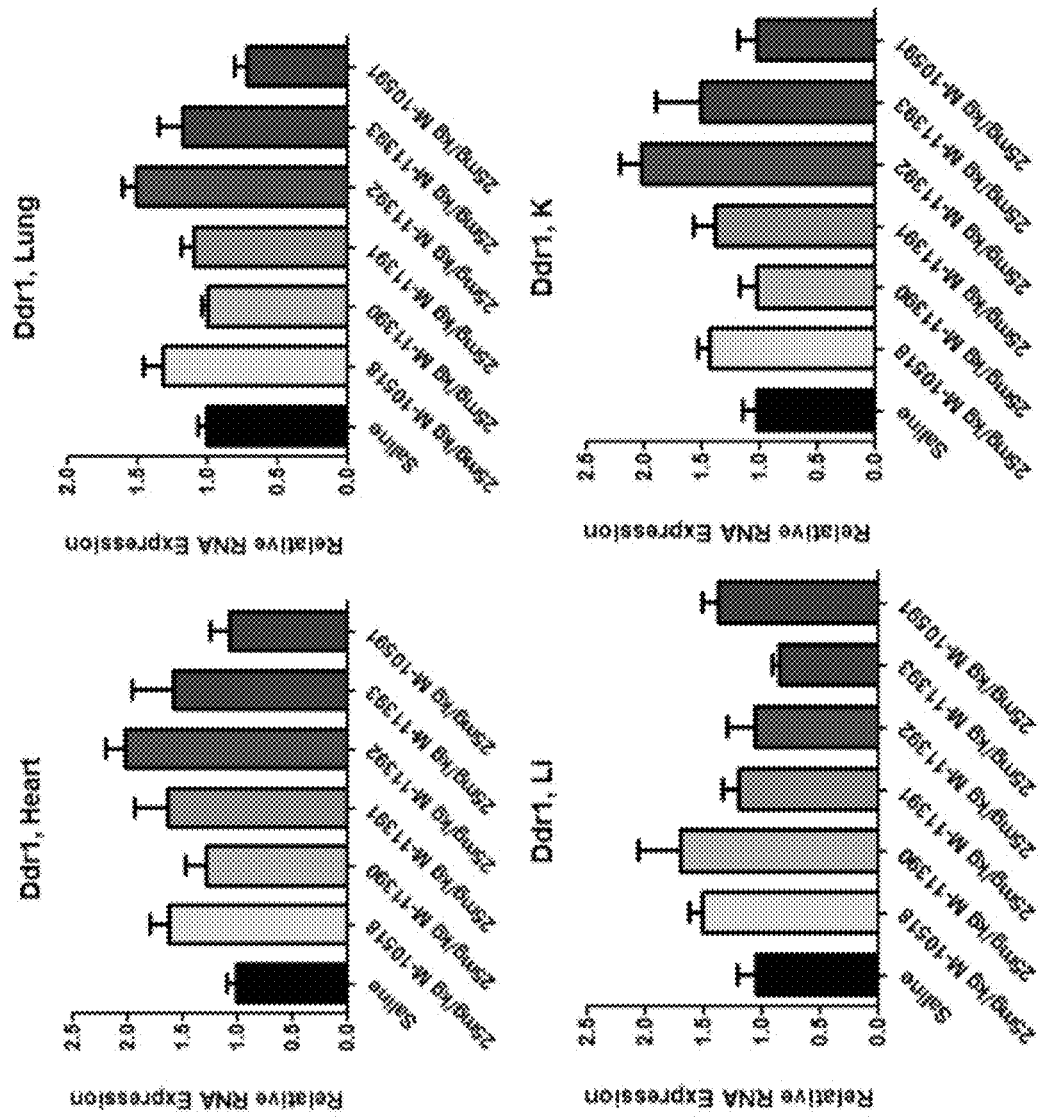

To determine if miR-199a inhibition correlated to in vivo efficacy, we assessed the miR-199 target, Ddr1 for de-repression by performing real-time PCR. Surprisingly, all antimiRs targeting miR-199a appeared to show Ddr1 target de-repression in the heart with the exception of M-11390 (FIG. 5C). For other tissues, different compounds showed varying degrees of target regulation, however, M-10518 (which is the M-10101 motif) consistently appeared to show target de-repression for all tissues, suggesting this motif confers cardiac and multi-tissue efficacy in vivo.

Example 6

In Vivo Efficacy of AntimiR-92a

Three antimiRs against miR-92a with LNA and DNA placements similar to those found for the miR-208a screen were synthesized to determine if this motif confers efficacy in further miRNA families. The sequence and modification patterns of these antimiRs with their corresponding predicted Tm values are depicted in Table 9 below (description of notations is as described in Table 4). The M-11127 compound contains the same LNA and DNA placements as M-10101 (antimiR-208a), M-10707 (antimiR-208b), M-11192 (antimiR-378), M-11185 (antimiR-29), and M-10518 (antimiR-199a).

TABLE 9

| Molecule # | Alias | Sequence | Length | LNA/DNA | Predicted Tm |
|---|---|---|---|---|---|
| 10338 | 92a_LNA_16_PS | lCs; dCs; lGs; dGs; dGs; lAs; dCs; lAs; dAs; lGs; lTs; dGs; lCs; lAs; dAs; lT (SEQ ID NO: 120) | 16 | 9/7 | 85 |
| 11127 | 92a_LNA_16_1 | lCs; dCs; dGs; dGs; dGs; lAs; dCs; lAs; dAs; lGs; lTs; dGs; lCs; dAs; lAs; lT (SEQ ID NO: 121) | 16 | 9/7 | 89 |
| 11130 | 92a_LNA_16_4 | lCs; dCs; lGs; dGs; dGs; lAs; dCs; dAs; lAs; lGs; lTs; dGs; lCs; lAs; dAs; lT (SEQ ID NO: 122) | 16 | 9/7 | 86 |

Figure 6:
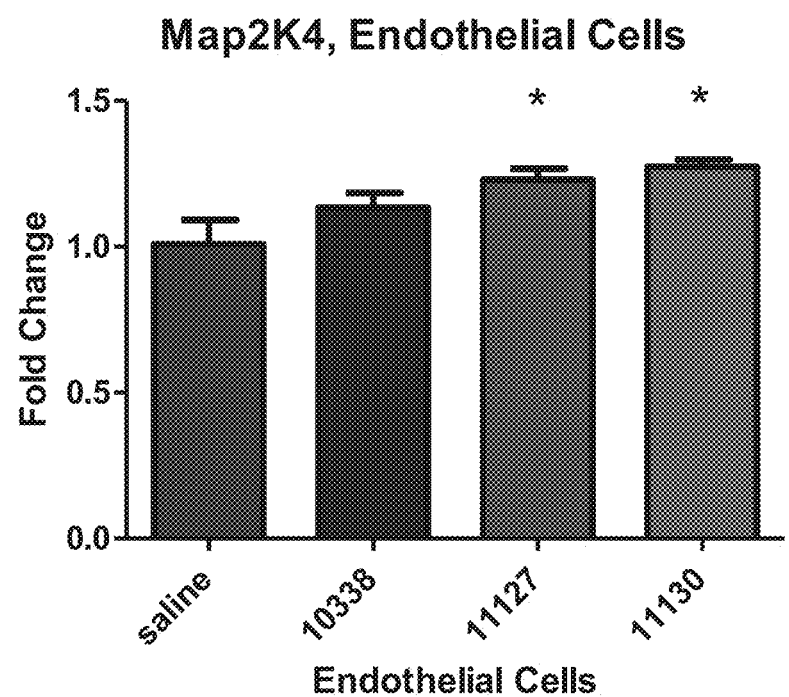
FIG. 6. Real-time PGR from endothelial cells isolated from heart tissue of antimiR-92a-treated rats showed differing target de-repression in vivo using Map2K4 as a primary readout for efficacy and target de-repression. *p<0.05 vs. Saline.

These antimiRs were dorsally injected into 6-8 week old Sprague Dawley rats subcutaneously at a dose of 25 mg/kg (n=4 per group). Injection volume was 1.0 mL. Two days after a single dose, these rats were sacrificed and endothelial cells from the heart were collected for molecular analysis including miRNA inhibition and target de-repression. RNA was isolated from endothelial cells and real-time PGR was performed to assess de-repression of the miR-92a target, Map2K4. Administration of antimiR M-11127 (which is the M-10101 motif) as well as antimiR M-11130 resulted in a significant increase in Map2K4 expression in endothelial cells (FIG. 6), demonstrating that these two inhibitors have in vivo efficacy.

The invention claimed is:

1. An oligonucleotide comprising a sequence of 16 nucleotides, wherein the sequence is complementary to a miRNA and comprises no more than three contiguous locked nucleic acids (LNAs), wherein from the 5' end to the 3' end, positions 1, 5, 8, 10, and 16 of the sequence are LNAs, and wherein the miRNA is not miR-208a, miR-208b, or miR-499.

2. The oligonucleotide of claim 1, wherein from the 5' end to the 3' end, the sequence further comprises LNAs at positions 6, 11, 13, and 15.

3. The oligonucleotide of claim 1, wherein at least one of the non-locked nucleotides is 2' deoxy, 2' O-alkyl, or 2' halo.

4. The oligonucleotide of claim 1, wherein all of the non-locked nucleotides are 2' deoxy.

5. The oligonucleotide of claim 1, wherein at least one LNA has a 2' to 4' methylene bridge.

6. The oligonucleotide of claim 1, wherein the oligonucleotide has a 5' cap structure, 3' cap structure, or 5' and 3' cap structure.

7. The oligonucleotide of claim 1, wherein the oligonucleotide comprises one or more phosphorothioate linkages.

8. The oligonucleotide of claim 7, wherein the oligonucleotide is fully phosphorothioate-linked.

9. The oligonucleotide of claim 1, further comprising a pendent lipophilic or hydrophilic group.

10. The oligonucleotide of claim 1, wherein the miRNA is expressed in cardiac tissue.

11. The oligonucleotide of claim 1, wherein the miRNA is miR-15a, miR-15b, miR-16-1, miR-16-2, miR-24, miR-25, miR-26a, miR-497, miR-195, miR-424, a let 7 family member, miR-21, miR-199a-b, miR-214, miR-10a-b, miR-16, miR-125b, miR-146a-b, miR-221, miR-222, a miR-30 family member, miR-126, miR-133, miR-1, miR-143, miR-145, miR-486, miR-92a, miR-320, miR-1-1, miR-1-2, miR-451, miR-378, miR-378*, miR-92, miR-34a, miR-34b, miR-34c, miR-29, or miR-33.

12. A pharmaceutical composition comprising an effective amount of the oligonucleotide of claim 1, or a pharmaceutically-acceptable salt thereof, and a pharmaceutically-acceptable carrier or diluent.

13. The pharmaceutical composition of claim 12, wherein the pharmaceutically-acceptable carrier comprises a colloidal dispersion system, macromolecular complex, nanocapsule, nanoparticle, microsphere, bead, oil-in-water emulsion, micelle, mixed micelle, or liposome.

14. The pharmaceutical composition of claim 12, wherein the pharmaceutically-acceptable carrier or diluent consists essentially of saline.

* * * * *

SEQUENCE LISTING

<160> NUMBER OF SEQ ID NOS: 122

<210> SEQ ID NO 1
<211> LENGTH: 22
<212> TYPE: RNA
<213> ORGANISM: Homo sapiens

```
<400> SEQUENCE: 1
uggaauguaa agaaguaugu au                                    22

<210> SEQ ID NO 2
<211> LENGTH: 22
<212> TYPE: RNA
<213> ORGANISM: Homo sapiens

<400> SEQUENCE: 2
aacccguaga uccgaacuug ug                                    22

<210> SEQ ID NO 3
<211> LENGTH: 23
<212> TYPE: RNA
<213> ORGANISM: Homo sapiens

<400> SEQUENCE: 3
uacccuguag auccgaauuu gug                                   23

<210> SEQ ID NO 4
<211> LENGTH: 23
<212> TYPE: RNA
<213> ORGANISM: Homo sapiens

<400> SEQUENCE: 4
uacccuguag aaccgaauuu gug                                   23

<210> SEQ ID NO 5
<211> LENGTH: 22
<212> TYPE: RNA
<213> ORGANISM: Homo sapiens

<400> SEQUENCE: 5
ucccugagac ccuaacuugu ga                                    22

<210> SEQ ID NO 6
<211> LENGTH: 22
<212> TYPE: RNA
<213> ORGANISM: Homo sapiens

<400> SEQUENCE: 6
ucguaccgug aguaauaaug cg                                    22

<210> SEQ ID NO 7
<211> LENGTH: 21
<212> TYPE: RNA
<213> ORGANISM: Homo sapiens

<400> SEQUENCE: 7
ucacagugaa ccggucucuu u                                     21

<210> SEQ ID NO 8
<211> LENGTH: 22
<212> TYPE: RNA
<213> ORGANISM: Homo sapiens

<400> SEQUENCE: 8
uuuggucccc uucaaccagc ug                                    22

<210> SEQ ID NO 9
<211> LENGTH: 22
<212> TYPE: RNA
<213> ORGANISM: Homo sapiens
```

```
<400> SEQUENCE: 9 uuugguccccc uucaaccagc ua                                              22

<210> SEQ ID NO 10
<211> LENGTH: 22
<212> TYPE: RNA
<213> ORGANISM: Homo sapiens

<400> SEQUENCE: 10
ucuacagugc acgugucucc ag                                               22

<210> SEQ ID NO 11
<211> LENGTH: 21
<212> TYPE: RNA
<213> ORGANISM: Homo sapiens

<400> SEQUENCE: 11
ugagaugaag cacuguagcu c                                                21

<210> SEQ ID NO 12
<211> LENGTH: 23
<212> TYPE: RNA
<213> ORGANISM: Homo sapiens

<400> SEQUENCE: 12
guccaguuuu cccaggaauc ccu                                              23

<210> SEQ ID NO 13
<211> LENGTH: 22
<212> TYPE: RNA
<213> ORGANISM: Homo sapiens

<400> SEQUENCE: 13
ugagaacuga auuccauggg uu                                               22

<210> SEQ ID NO 14
<211> LENGTH: 22
<212> TYPE: RNA
<213> ORGANISM: Homo sapiens

<400> SEQUENCE: 14
ugagaacuga auuccauagg cu                                               22

<210> SEQ ID NO 15
<211> LENGTH: 22
<212> TYPE: RNA
<213> ORGANISM: Homo sapiens

<400> SEQUENCE: 15
ucucccaacc cuuguaccag ug                                               22

<210> SEQ ID NO 16
<211> LENGTH: 22
<212> TYPE: RNA
<213> ORGANISM: Homo sapiens

<400> SEQUENCE: 16
uagcagcaca uaaugguuug ug                                               22

<210> SEQ ID NO 17
<211> LENGTH: 22
<212> TYPE: RNA
```

```
<213> ORGANISM: Homo sapiens

<400> SEQUENCE: 17
uagcagcaca ucaugguuua ca                                           22

<210> SEQ ID NO 18
<211> LENGTH: 22
<212> TYPE: RNA
<213> ORGANISM: Homo sapiens

<400> SEQUENCE: 18
uagcagcacg uaaauauugg cg                                           22

<210> SEQ ID NO 19
<211> LENGTH: 23
<212> TYPE: RNA
<213> ORGANISM: Homo sapiens

<400> SEQUENCE: 19
aacauucauu gcugucggug ggu                                          23

<210> SEQ ID NO 20
<211> LENGTH: 21
<212> TYPE: RNA
<213> ORGANISM: Homo sapiens

<400> SEQUENCE: 20
uagcagcaca gaaauauugg c                                            21

<210> SEQ ID NO 21
<211> LENGTH: 22
<212> TYPE: RNA
<213> ORGANISM: Homo sapiens

<400> SEQUENCE: 21
uucaccaccu ucuccaccca gc                                           22

<210> SEQ ID NO 22
<211> LENGTH: 23
<212> TYPE: RNA
<213> ORGANISM: Homo sapiens

<400> SEQUENCE: 22
cccaguguuc agacuaccug uuc                                          23

<210> SEQ ID NO 23
<211> LENGTH: 23
<212> TYPE: RNA
<213> ORGANISM: Homo sapiens

<400> SEQUENCE: 23
cccaguguuu agacuaucug uuc                                          23

<210> SEQ ID NO 24
<211> LENGTH: 22
<212> TYPE: RNA
<213> ORGANISM: Homo sapiens

<400> SEQUENCE: 24
acaguagucu gcacauuggu ua                                           22

<210> SEQ ID NO 25
<211> LENGTH: 22
```

```
<212> TYPE: RNA
<213> ORGANISM: Homo sapiens

<400> SEQUENCE: 25
auaagacgag caaaaagcuu gu                                              22

<210> SEQ ID NO 26
<211> LENGTH: 22
<212> TYPE: RNA
<213> ORGANISM: Homo sapiens

<400> SEQUENCE: 26
auaagacgaa caaaagguuu gu                                              22

<210> SEQ ID NO 27
<211> LENGTH: 23
<212> TYPE: RNA
<213> ORGANISM: Homo sapiens

<400> SEQUENCE: 27
uaaagugcuu auagugcagg uag                                             23

<210> SEQ ID NO 28
<211> LENGTH: 22
<212> TYPE: RNA
<213> ORGANISM: Homo sapiens

<400> SEQUENCE: 28
uagcuuauca gacugauguu ga                                              22

<210> SEQ ID NO 29
<211> LENGTH: 22
<212> TYPE: RNA
<213> ORGANISM: Homo sapiens

<400> SEQUENCE: 29
acagcaggca cagacaggca gu                                              22

<210> SEQ ID NO 30
<211> LENGTH: 22
<212> TYPE: RNA
<213> ORGANISM: Homo sapiens

<400> SEQUENCE: 30
aagcugccag uugaagaacu gu                                              22

<210> SEQ ID NO 31
<211> LENGTH: 23
<212> TYPE: RNA
<213> ORGANISM: Homo sapiens

<400> SEQUENCE: 31
agcuacauug ucugcugggu uuc                                             23

<210> SEQ ID NO 32
<211> LENGTH: 21
<212> TYPE: RNA
<213> ORGANISM: Homo sapiens

<400> SEQUENCE: 32
agcuacaucu ggcuacuggg u                                               21

<210> SEQ ID NO 33
```

```
<211> LENGTH: 21
<212> TYPE: RNA
<213> ORGANISM: Homo sapiens

<400> SEQUENCE: 33
caagucacua gugguuccgu u                                              21

<210> SEQ ID NO 34
<211> LENGTH: 21
<212> TYPE: RNA
<213> ORGANISM: Homo sapiens

<400> SEQUENCE: 34
aucacauugc cagggauuuc c                                              21

<210> SEQ ID NO 35
<211> LENGTH: 22
<212> TYPE: RNA
<213> ORGANISM: Homo sapiens

<400> SEQUENCE: 35
uggcucaguu cagcaggaac ag                                             22

<210> SEQ ID NO 36
<211> LENGTH: 22
<212> TYPE: RNA
<213> ORGANISM: Homo sapiens

<400> SEQUENCE: 36
cauugcacuu gucucggucu ga                                             22

<210> SEQ ID NO 37
<211> LENGTH: 22
<212> TYPE: RNA
<213> ORGANISM: Homo sapiens

<400> SEQUENCE: 37
uucaaguaau ccaggauagg cu                                             22

<210> SEQ ID NO 38
<211> LENGTH: 21
<212> TYPE: RNA
<213> ORGANISM: Homo sapiens

<400> SEQUENCE: 38
uucaaguaau ucaggauagg u                                              21

<210> SEQ ID NO 39
<211> LENGTH: 22
<212> TYPE: RNA
<213> ORGANISM: Homo sapiens

<400> SEQUENCE: 39
aaggagcuca cagucuauug ag                                             22

<210> SEQ ID NO 40
<211> LENGTH: 22
<212> TYPE: RNA
<213> ORGANISM: Homo sapiens

<400> SEQUENCE: 40
uagcaccauc ugaaaucggu ua                                             22
```

```
<210> SEQ ID NO 41
<211> LENGTH: 23
<212> TYPE: RNA
<213> ORGANISM: Homo sapiens

<400> SEQUENCE: 41
uagcaccauu ugaaaucagu guu                                              23

<210> SEQ ID NO 42
<211> LENGTH: 22
<212> TYPE: RNA
<213> ORGANISM: Homo sapiens

<400> SEQUENCE: 42
uagcaccauu ugaaaucggu ua                                               22

<210> SEQ ID NO 43
<211> LENGTH: 22
<212> TYPE: RNA
<213> ORGANISM: Homo sapiens

<400> SEQUENCE: 43
uguaaacauc cucgacugga ag                                               22

<210> SEQ ID NO 44
<211> LENGTH: 22
<212> TYPE: RNA
<213> ORGANISM: Homo sapiens

<400> SEQUENCE: 44
uguaaacauc cuacacucag cu                                               22

<210> SEQ ID NO 45
<211> LENGTH: 23
<212> TYPE: RNA
<213> ORGANISM: Homo sapiens

<400> SEQUENCE: 45
uguaaacauc cuacacucuc agc                                              23

<210> SEQ ID NO 46
<211> LENGTH: 22
<212> TYPE: RNA
<213> ORGANISM: Homo sapiens

<400> SEQUENCE: 46
uguaaacauc cccgacugga ag                                               22

<210> SEQ ID NO 47
<211> LENGTH: 22
<212> TYPE: RNA
<213> ORGANISM: Homo sapiens

<400> SEQUENCE: 47
uguaaacauc cuugacugga ag                                               22

<210> SEQ ID NO 48
<211> LENGTH: 21
<212> TYPE: RNA
<213> ORGANISM: Homo sapiens

<400> SEQUENCE: 48
gugcauugua guugcauugc a                                                21
```

```
<210> SEQ ID NO 49
<211> LENGTH: 20
<212> TYPE: RNA
<213> ORGANISM: Homo sapiens

<400> SEQUENCE: 49
gugcauugcu uugcauugc                                                    20

<210> SEQ ID NO 50
<211> LENGTH: 22
<212> TYPE: RNA
<213> ORGANISM: Homo sapiens

<400> SEQUENCE: 50
uggcaguguc uuagcugguu gu                                                22

<210> SEQ ID NO 51
<211> LENGTH: 22
<212> TYPE: RNA
<213> ORGANISM: Homo sapiens

<400> SEQUENCE: 51
caaucacuaa cuccacugcc au                                                22

<210> SEQ ID NO 52
<211> LENGTH: 23
<212> TYPE: RNA
<213> ORGANISM: Homo sapiens

<400> SEQUENCE: 52
aggcagugua guuagcugau ugc                                               23

<210> SEQ ID NO 53
<211> LENGTH: 22
<212> TYPE: RNA
<213> ORGANISM: Homo sapiens

<400> SEQUENCE: 53
aaaagcuggg uugagagggc ga                                                22

<210> SEQ ID NO 54
<211> LENGTH: 23
<212> TYPE: RNA
<213> ORGANISM: Homo sapiens

<400> SEQUENCE: 54
ucucacacag aaaucgcacc cgu                                               23

<210> SEQ ID NO 55
<211> LENGTH: 22
<212> TYPE: RNA
<213> ORGANISM: Homo sapiens

<400> SEQUENCE: 55
gaaguuguuc gugguggauu cg                                                22

<210> SEQ ID NO 56
<211> LENGTH: 22
<212> TYPE: RNA
<213> ORGANISM: Homo sapiens

<400> SEQUENCE: 56
acuggacuua gggucagaag gc                                                22
```

```
<210> SEQ ID NO 57
<211> LENGTH: 21
<212> TYPE: RNA
<213> ORGANISM: Homo sapiens

<400> SEQUENCE: 57
acuggacuug gagucagaag g                                              21

<210> SEQ ID NO 58
<211> LENGTH: 22
<212> TYPE: RNA
<213> ORGANISM: Homo sapiens

<400> SEQUENCE: 58
cuccugacuc cagguccugu gu                                             22

<210> SEQ ID NO 59
<211> LENGTH: 22
<212> TYPE: RNA
<213> ORGANISM: Homo sapiens

<400> SEQUENCE: 59
cagcagcaau ucauguuuug aa                                             22

<210> SEQ ID NO 60
<211> LENGTH: 22
<212> TYPE: RNA
<213> ORGANISM: Homo sapiens

<400> SEQUENCE: 60
aaaccguuac cauuacugag uu                                             22

<210> SEQ ID NO 61
<211> LENGTH: 21
<212> TYPE: RNA
<213> ORGANISM: Homo sapiens

<400> SEQUENCE: 61
ucacuccucu ccucccgucu u                                              21

<210> SEQ ID NO 62
<211> LENGTH: 22
<212> TYPE: RNA
<213> ORGANISM: Homo sapiens

<400> SEQUENCE: 62
ucaggcucag uccccucccg au                                             22

<210> SEQ ID NO 63
<211> LENGTH: 22
<212> TYPE: RNA
<213> ORGANISM: Homo sapiens

<400> SEQUENCE: 63
uccuguacug agcugccccg ag                                             22

<210> SEQ ID NO 64
<211> LENGTH: 21
<212> TYPE: RNA
<213> ORGANISM: Homo sapiens

<400> SEQUENCE: 64
```

```
cagcagcaca cuguggeuuug u                                              21

<210> SEQ ID NO 65
<211> LENGTH: 21
<212> TYPE: RNA
<213> ORGANISM: Homo sapiens

<400> SEQUENCE: 65
uuaagacuug cagugauguu u                                               21

<210> SEQ ID NO 66
<211> LENGTH: 23
<212> TYPE: RNA
<213> ORGANISM: Homo sapiens

<400> SEQUENCE: 66
ucggggauca ucaugucacg aga                                             23

<210> SEQ ID NO 67
<211> LENGTH: 22
<212> TYPE: RNA
<213> ORGANISM: Homo sapiens

<400> SEQUENCE: 67
uauugcacuu gucccggccu gu                                              22

<210> SEQ ID NO 68
<211> LENGTH: 22
<212> TYPE: RNA
<213> ORGANISM: Homo sapiens

<400> SEQUENCE: 68
uauugcacuc gucccggccu cc                                              22

<210> SEQ ID NO 69
<211> LENGTH: 22
<212> TYPE: RNA
<213> ORGANISM: Homo sapiens

<400> SEQUENCE: 69
ugagguagua gguuguauag uu                                              22

<210> SEQ ID NO 70
<211> LENGTH: 22
<212> TYPE: RNA
<213> ORGANISM: Homo sapiens

<400> SEQUENCE: 70
ugagguagua gguugugugg uu                                              22

<210> SEQ ID NO 71
<211> LENGTH: 22
<212> TYPE: RNA
<213> ORGANISM: Homo sapiens

<400> SEQUENCE: 71
ugagguagua gguuguaugg uu                                              22

<210> SEQ ID NO 72
<211> LENGTH: 22
<212> TYPE: RNA
<213> ORGANISM: Homo sapiens

<400> SEQUENCE: 72
```
agagguagua gguugcauag uu                                            22

<210> SEQ ID NO 73
<211> LENGTH: 22
<212> TYPE: RNA
<213> ORGANISM: Homo sapiens

<400> SEQUENCE: 73
ugagguagga gguuguauag uu                                            22

<210> SEQ ID NO 74
<211> LENGTH: 22
<212> TYPE: RNA
<213> ORGANISM: Homo sapiens

<400> SEQUENCE: 74
ugagguagua gauuguauag uu                                            22

<210> SEQ ID NO 75
<211> LENGTH: 22
<212> TYPE: RNA
<213> ORGANISM: Homo sapiens

<400> SEQUENCE: 75
ugagguagua guuuguacag uu                                            22

<210> SEQ ID NO 76
<211> LENGTH: 16
<212> TYPE: DNA
<213> ORGANISM: Artificial Sequence
<220> FEATURE:
<223> OTHER INFORMATION: Modified antimiR-208a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(4)
<223> OTHER INFORMATION: May be a phosphorothioate thymidine
<220> FEATURE:
<221> NAME/KEY: MOD_RES
<222> LOCATION: (5)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a locked nucleic acid phosphorothioate
      guanosine
<220> FEATURE:
<221> NAME/KEY: MOD_RES

```
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 76 cttttgctc gtctta                                                      16

<210> SEQ ID NO 77
<211> LENGTH: 16
<212> TYPE: DNA
<213> ORGANISM: Artificial Sequence
<220> FEATURE:
<223> OTHER INFORMATION: Modified antimiR-208a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
```

```
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(15)
<223> OTHER INFORMATION: May be a locked nucleic acid phosphorothioate
      thymidine

<400> SEQUENCE: 77 cttttttgctc gtctta                                                    16

<210> SEQ ID NO 78
<211> LENGTH: 16
<212> TYPE: DNA
<213> ORGANISM: Artificial Sequence
<220> FEATURE:
<223> OTHER INFORMATION: Modified antimiR-208a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 78
``` cttttttgctc gtctta 16

<210> SEQ ID NO 79
<211> LENGTH: 16
<212> TYPE: DNA
<213> ORGANISM: Artificial Sequence
<220> FEATURE:
<223> OTHER INFORMATION: Modified antimiR-208a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate thymidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      thymidine

<400> SEQUENCE: 79
ctttttgctc gtctta 16

```
<210> SEQ ID NO 80
<211> LENGTH: 16
<212> TYPE: DNA
<213> ORGANISM: Artificial Sequence
<220> FEATURE:
<223> OTHER INFORMATION: Modified antimiR-208a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      guanosine
<220> FEATURE:
<221> NAME/KEY: MOD_RES
<222> LOCATION: (8)..(8)
<223> OTHER INFORMATION: May be a phosphorothioate cytidine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a phosphorothioate cytidine
<220> FEATURE:
<221> NAME/KEY: MOD_RES
<222> LOCATION: (11)..(11)
<223> OTHER INFORMATION: May be a locked nucleic acid phosphorothioate
      guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a locked nucleic acid adenosine
```

<400> SEQUENCE: 80 cttttgctc gtctta 16

<210> SEQ ID NO 81
<211> LENGTH: 16
<212> TYPE: DNA
<213> ORGANISM: Artificial Sequence
<220> FEATURE:
<223> OTHER INFORMATION: Modified antimiR-208a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(3)
<223> OTHER INFORMATION: May be a phosphorothioate thymidine
<220> FEATURE:
<221> NAME/KEY: MOD_RES
<222> LOCATION: (4)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      guanosine
<220> FEATURE:
<221> NAME/KEY: MOD_RES
<222> LOCATION: (8)..(8)
<223> OTHER INFORMATION: May be a phosphorothioate cytidine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 81 cttttgctc gtctta 16

```
<210> SEQ ID NO 82
<211> LENGTH: 16
<212> TYPE: DNA
<213> ORGANISM: Artificial Sequence
<220> FEATURE:
<223> OTHER INFORMATION: Modified antimiR-208a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      thymidine

<400> SEQUENCE: 82 cttttgctc gtctta                                                  16

<210> SEQ ID NO 83
<211> LENGTH: 16
<212> TYPE: DNA
<213> ORGANISM: Artificial Sequence
<220> FEATURE:
<223> OTHER INFORMATION: Modified antimiR-208a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
```

```
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(4)
<223> OTHER INFORMATION: May be a locked nucleic acid phosphorothioate
      thymidine
<220> FEATURE:
<221> NAME/KEY: MOD_RES
<222> LOCATION: (5)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      guanosine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 83 cttttttgctc gtctta                                                    16

<210> SEQ ID NO 84
<211> LENGTH: 16
<212> TYPE: DNA
<213> ORGANISM: Artificial Sequence
<220> FEATURE:
<223> OTHER INFORMATION: Modified antimiR-208a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(4)
<223> OTHER INFORMATION: May be a phosphorothioate thymidine
```

```
<220> FEATURE:
<221> NAME/KEY: MOD_RES
<222> LOCATION: (5)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a phosphorothioate cytidine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a locked nucleic acid phosphorothioate
      guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 84 cttttttgctc gtctta                                                    16

<210> SEQ ID NO 85
<211> LENGTH: 16
<212> TYPE: DNA
<213> ORGANISM: Artificial Sequence
<220> FEATURE:
<223> OTHER INFORMATION: Modified antimiR-208a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(5)
<223> OTHER INFORMATION: May be a phosphorothioate thymidine
<220> FEATURE:
<221> NAME/KEY: MOD_RES
<222> LOCATION: (6)..(6)
```

```
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a locked nucleic acid phosphorothioate
      guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 85 cttttttgctc gtctta                                                    16

<210> SEQ ID NO 86
<211> LENGTH: 16
<212> TYPE: DNA
<213> ORGANISM: Artificial Sequence
<220> FEATURE:
<223> OTHER INFORMATION: Modified antimiR-208a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(5)
<223> OTHER INFORMATION: May be a phosphorothioate thymidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
```

<221> NAME/KEY: MOD_RES
<222> LOCATION: (7)..(7)
<223> OTHER INFORMATION: May be a locked nucleic acid phosphorothioate
      guanosine
<220> FEATURE:
<221> NAME/KEY: MOD_RES
<222> LOCATION: (8)..(8)
<223> OTHER INFORMATION: May be a phosphorothioate cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a locked nucleic acid phosphorothioate
      guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 86 cttttttgctc gtctta                                                  16

<210> SEQ ID NO 87
<211> LENGTH: 16
<212> TYPE: DNA
<213> ORGANISM: Artificial Sequence
<220> FEATURE:
<223> OTHER INFORMATION: Modified antimiR-208a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(4)
<223> OTHER INFORMATION: May be a phosphorothioate thymidine
<220> FEATURE:
<221> NAME/KEY: MOD_RES
<222> LOCATION: (5)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      cytidine

```
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a locked nucleic acid phosphorothioate
      guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 87 cttttttgctc gtctta                                                   16

<210> SEQ ID NO 88
<211> LENGTH: 16
<212> TYPE: DNA
<213> ORGANISM: Artificial Sequence
<220> FEATURE:
<223> OTHER INFORMATION: Modified antimiR-208a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
```

```
             cytidine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 88 cttttttgctc gtctta                                                    16

<210> SEQ ID NO 89
<211> LENGTH: 16
<212> TYPE: DNA
<213> ORGANISM: Artificial Sequence
<220> FEATURE:
<223> OTHER INFORMATION: Modified antimiR-208a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
```

-continued

```
<223> OTHER INFORMATION: May be a locked nucleic acid phosphorothioate
      guanosine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 89 cttttttgctc gtctta                                                    16

<210> SEQ ID NO 90
<211> LENGTH: 16
<212> TYPE: DNA
<213> ORGANISM: Artificial Sequence
<220> FEATURE:
<223> OTHER INFORMATION: Modified antimiR-208a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(3)
<223> OTHER INFORMATION: May be a phosphorothioate thymidine
<220> FEATURE:
<221> NAME/KEY: MOD_RES
<222> LOCATION: (4)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      guanosine
<220> FEATURE:
<221> NAME/KEY: MOD_RES
```

```
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 90 cttttttgctc gtctta                                                    16

<210> SEQ ID NO 91
<211> LENGTH: 16
<212> TYPE: DNA
<213> ORGANISM: Artificial Sequence
<220> FEATURE:
<223> OTHER INFORMATION: Modified antimiR-208a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      guanosine
<220> FEATURE:
```

```
<221> NAME/KEY: MOD_RES
<222> LOCATION: (8)..(8)
<223> OTHER INFORMATION: May be a phosphorothioate cytidine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 91 cttttttgctc gtctta                                                    16

<210> SEQ ID NO 92
<211> LENGTH: 16
<212> TYPE: DNA
<213> ORGANISM: Artificial Sequence
<220> FEATURE:
<223> OTHER INFORMATION: Modified antimiR-208b oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(4)
<223> OTHER INFORMATION: May be a phosphorothioate thymidine
<220> FEATURE:
<221> NAME/KEY: MOD_RES
<222> LOCATION: (5)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      thymidine
<220> FEATURE:
```

<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a locked nucleic acid phosphorothioate
      guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 92
cctttTgttc gtctta                                                 16

<210> SEQ ID NO 93
<211> LENGTH: 16
<212> TYPE: DNA
<213> ORGANISM: Artificial Sequence
<220> FEATURE:
<223> OTHER INFORMATION: Modified antimiR-208b oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      thymidine

```
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(15)
<223> OTHER INFORMATION: May be a locked nucleic acid phosphorothioate
      thymidine

<400> SEQUENCE: 93 cctttgttc gtctta                                                      16

<210> SEQ ID NO 94
<211> LENGTH: 16
<212> TYPE: DNA
<213> ORGANISM: Artificial Sequence
<220> FEATURE:
<223> OTHER INFORMATION: Modified antimiR-208b oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      thymidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a phosphorothioate thymidine
```

```
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 94 cctttttgttc gtctta                                                  16

<210> SEQ ID NO 95
<211> LENGTH: 16
<212> TYPE: DNA
<213> ORGANISM: Artificial Sequence
<220> FEATURE:
<223> OTHER INFORMATION: Modified antimiR-208b oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate thymidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
```

-continued

```
<220> FEATURE:
<221> NAME/KEY: MOD_RES
<222> LOCATION: (15)..(15)
<223> OTHER INFORMATION: May be a locked nucleic acid phosphorothioate
      thymidine

<400> SEQUENCE: 95 cctttttgttc gtctta                                                        16

<210> SEQ ID NO 96
<211> LENGTH: 16
<212> TYPE: DNA
<213> ORGANISM: Artificial Sequence
<220> FEATURE:
<223> OTHER INFORMATION: Modified antimiR-208b oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      guanosine
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a phosphorothioate cytidine
<220> FEATURE:
<221> NAME/KEY: MOD_RES
<222> LOCATION: (11)..(11)
<223> OTHER INFORMATION: May be a locked nucleic acid phosphorothioate
      guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
```

```
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 96 cctttttgttc gtctta                                                        16

<210> SEQ ID NO 97
<211> LENGTH: 16
<212> TYPE: DNA
<213> ORGANISM: Artificial Sequence
<220> FEATURE:
<223> OTHER INFORMATION: Modified antimiR-208b oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(3)
<223> OTHER INFORMATION: May be a phosphorothioate thymidine
<220> FEATURE:
<221> NAME/KEY: MOD_RES
<222> LOCATION: (4)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      guanosine
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(14)
```

```
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 97 cctttttgttc gtctta                                                      16

<210> SEQ ID NO 98
<211> LENGTH: 16
<212> TYPE: DNA
<213> ORGANISM: Artificial Sequence
<220> FEATURE:
<223> OTHER INFORMATION: Modified antimiR-208b oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      thymidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      thymidine

<400> SEQUENCE: 98
```
ccttttgttc gtctta 16

<210> SEQ ID NO 99
<211> LENGTH: 16
<212> TYPE: DNA
<213> ORGANISM: Artificial Sequence
<220> FEATURE:
<223> OTHER INFORMATION: Modified antimiR-208b oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(4)
<223> OTHER INFORMATION: May be a locked nucleic acid phosphorothioate
      thymidine
<220> FEATURE:
<221> NAME/KEY: MOD_RES
<222> LOCATION: (5)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      guanosine
<220> FEATURE:
<221> NAME/KEY: MOD_RES
<222> LOCATION: (8)..(8)
<223> OTHER INFORMATION: May be a locked nucleic acid phosphorothioate
      thymidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 99
ccttttgttc gtctta 16

<210> SEQ ID NO 100

```
<211> LENGTH: 16
<212> TYPE: DNA
<213> ORGANISM: Artificial Sequence
<220> FEATURE:
<223> OTHER INFORMATION: Modified antimiR-208b oligonucleotide
<220> FEATURE:
<221> NAME/KEY: MOD_RES
<222> LOCATION: (1)..(2)
<223> OTHER INFORMATION: May be a locked nucleic acid phosphorothioate
      cytidine
<220> FEATURE:
<221> NAME/KEY: MOD_RES
<222> LOCATION: (3)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      guanosine
<220> FEATURE:
<221> NAME/KEY: MOD_RES
<222> LOCATION: (8)..(8)
<223> OTHER INFORMATION: May be a locked nucleic acid phosphorothioate
      thymidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 100 cctttgttc gtctta                                                      16

<210> SEQ ID NO 101
<211> LENGTH: 16
<212> TYPE: DNA
<213> ORGANISM: Artificial Sequence
<220> FEATURE:
```

```
<223> OTHER INFORMATION: Modified antimiR-378 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a phosphorothioate guanosine
<220> FEATURE:
<221> NAME/KEY: MOD_RES
<222> LOCATION: (4)..(4)
<223> OTHER INFORMATION: May be a phosphorothioate adenosine
<220> FEATURE:
<221> NAME/KEY: MOD_RES
<222> LOCATION: (5)..(5)
<223> OTHER INFORMATION: May be a locked nucleic acid phosphorothioate
      cytidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate cytidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate adenosine
<220> FEATURE:
<221> NAME/KEY: MOD_RES
<222> LOCATION: (10)..(10)
<223> OTHER INFORMATION: May be a locked nucleic acid phosphorothioate
      adenosine
<220> FEATURE:
<221> NAME/KEY: MOD_RES
<222> LOCATION: (11)..(11)
<223> OTHER INFORMATION: May be a locked nucleic acid phosphorothioate
      guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate cytidine
<220> FEATURE:
<221> NAME/KEY: MOD_RES
<222> LOCATION: (15)..(15)
<223> OTHER INFORMATION: May be a locked nucleic acid phosphorothioate
      adenosine
<220> FEATURE:
<221> NAME/KEY: MOD_RES
<222> LOCATION: (16)..(16)
<223> OTHER INFORMATION: May be a locked nucleic acid phosphorothioate
      guanosine

<400> SEQUENCE: 101
ctgactccaa gtccag                                                    16
```

```
<210> SEQ ID NO 102
<211> LENGTH: 16
<212> TYPE: DNA
<213> ORGANISM: Artificial Sequence
<220> FEATURE:
<223> OTHER INFORMATION: Modified antimiR-378 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      guanosine
<220> FEATURE:
<221> NAME/KEY: MOD_RES
<222> LOCATION: (4)..(4)
<223> OTHER INFORMATION: May be a locked nucleic acid phosphorothioate
      adenosine
<220> FEATURE:
<221> NAME/KEY: MOD_RES
<222> LOCATION: (5)..(5)
<223> OTHER INFORMATION: May be a locked nucleic acid phosphorothioate
      cytidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate cytidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate adenosine
<220> FEATURE:
<221> NAME/KEY: MOD_RES
<222> LOCATION: (10)..(10)
<223> OTHER INFORMATION: May be a locked nucleic acid phosphorothioate
      adenosine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate cytidine
<220> FEATURE:
<221> NAME/KEY: MOD_RES
<222> LOCATION: (15)..(15)
<223> OTHER INFORMATION: May be a phosphorothioate adenosine
<220> FEATURE:
<221> NAME/KEY: MOD_RES
<222> LOCATION: (16)..(16)
<223> OTHER INFORMATION: May be a locked nucleic acid phosphorothioate
``` guanosine

<400> SEQUENCE: 102
ctgactccaa gtccag                                                     16

<210> SEQ ID NO 103
<211> LENGTH: 16
<212> TYPE: DNA
<213> ORGANISM: Artificial Sequence
<220> FEATURE:
<223> OTHER INFORMATION: Modified antimiR-378 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      guanosine
<220> FEATURE:
<221> NAME/KEY: MOD_RES
<222> LOCATION: (4)..(4)
<223> OTHER INFORMATION: May be a locked nucleic acid phosphorothioate
      adenosine
<220> FEATURE:
<221> NAME/KEY: MOD_RES
<222> LOCATION: (5)..(5)
<223> OTHER INFORMATION: May be a phosphorothioate cytidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate cytidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a locked nucleic acid phosphorothioate
      adenosine
<220> FEATURE:
<221> NAME/KEY: MOD_RES
<222> LOCATION: (10)..(10)
<223> OTHER INFORMATION: May be a locked nucleic acid phosphorothioate
      adenosine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate cytidine
<220> FEATURE:
<221> NAME/KEY: MOD_RES
<222> LOCATION: (15)..(15)
<223> OTHER INFORMATION: May be a locked nucleic acid phosphorothioate
      adenosine
<220> FEATURE:
<221> NAME/KEY: MOD_RES
<222> LOCATION: (16)..(16)
<223> OTHER INFORMATION: May be a phosphorothioate guanosine

<400> SEQUENCE: 103
ctgactccaa gtccag                                                                16

<210> SEQ ID NO 104
<211> LENGTH: 16
<212> TYPE: DNA
<213> ORGANISM: Artificial Sequence
<220> FEATURE:
<223> OTHER INFORMATION: Modified antimiR-378 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      guanosine
<220> FEATURE:
<221> NAME/KEY: MOD_RES
<222> LOCATION: (4)..(4)
<223> OTHER INFORMATION: May be a phosphorothioate adenosine
<220> FEATURE:
<221> NAME/KEY: MOD_RES
<222> LOCATION: (5)..(5)
<223> OTHER INFORMATION: May be a locked nucleic acid phosphorothioate
      cytidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate cytidine
<220> FEATURE:
<221> NAME/KEY: MOD_RES
<222> LOCATION: (9)..(9)
<223> OTHER INFORMATION: May be a locked nucleic acid phosphorothioate
      adenosine
<220> FEATURE:
<221> NAME/KEY: MOD_RES
<222> LOCATION: (10)..(10)
<223> OTHER INFORMATION: May be a phosphorothioate adenosine
<220> FEATURE:
<221> NAME/KEY: MOD_RES
<222> LOCATION: (11)..(11)
<223> OTHER INFORMATION: May be a locked nucleic acid phosphorothioate
      guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:

<220> FEATURE:
<221> NAME/KEY: MOD_RES
<222> LOCATION: (14)..(14)
<223> OTHER INFORMATION: May be a phosphorothioate cytidine
<220> FEATURE:
<221> NAME/KEY: MOD_RES
<222> LOCATION: (15)..(15)
<223> OTHER INFORMATION: May be a locked nucleic acid phosphorothioate adenosine
<220> FEATURE:
<221> NAME/KEY: MOD_RES
<222> LOCATION: (16)..(16)
<223> OTHER INFORMATION: May be a locked nucleic acid phosphorothioate guanosine

<400> SEQUENCE: 104
ctgactccaa gtccag       16

<210> SEQ ID NO 105
<211> LENGTH: 16
<212> TYPE: DNA
<213> ORGANISM: Artificial Sequence
<220> FEATURE:
<223> OTHER INFORMATION: Modified antimiR-378 oligonucleotide
<220> FEATURE:
<221> NAME/KEY: MOD_RES
<222> LOCATION: (1)..(1)
<223> OTHER INFORMATION: May be a locked nucleic acid phosphorothioate cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a phosphorothioate guanosine
<220> FEATURE:
<221> NAME/KEY: MOD_RES
<222> LOCATION: (4)..(4)
<223> OTHER INFORMATION: May be a locked nucleic acid phosphorothioate adenosine
<220> FEATURE:
<221> NAME/KEY: MOD_RES
<222> LOCATION: (5)..(5)
<223> OTHER INFORMATION: May be a locked nucleic acid phosphorothioate cytidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate cytidine
<220> FEATURE:
<221> NAME/KEY: MOD_RES
<222> LOCATION: (8)..(8)
<223> OTHER INFORMATION: May be a phosphorothioate cytidine
<220> FEATURE:
<221> NAME/KEY: MOD_RES
<222> LOCATION: (9)..(10)
<223> OTHER INFORMATION: May be a locked nucleic acid phosphorothioate adenosine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate thymidine
<220> FEATURE:
<221> NAME/KEY: MOD_RES
<222> LOCATION: (13)..(13)
<223> OTHER INFORMATION: May be a phosphorothioate cytidine

```
<220> FEATURE:
<221> NAME/KEY: MOD_RES
<222> LOCATION: (14)..(14)
<223> OTHER INFORMATION: May be a locked nucleic acid phosphorothioate
      cytidine
<220> FEATURE:
<221> NAME/KEY: MOD_RES
<222> LOCATION: (15)..(15)
<223> OTHER INFORMATION: May be a phosphorothioate adenosine
<220> FEATURE:
<221> NAME/KEY: MOD_RES
<222> LOCATION: (16)..(16)
<223> OTHER INFORMATION: May be a locked nucleic acid phosphorothioate
      guanosine

<400> SEQUENCE: 105
ctgactccaa gtccag                                                      16

<210> SEQ ID NO 106
<211> LENGTH: 16
<212> TYPE: DNA
<213> ORGANISM: Artificial Sequence
<220> FEATURE:
<223> OTHER INFORMATION: Modified antimiR-378 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      guanosine
<220> FEATURE:
<221> NAME/KEY: MOD_RES
<222> LOCATION: (4)..(4)
<223> OTHER INFORMATION: May be a locked nucleic acid phosphorothioate
      adenosine
<220> FEATURE:
<221> NAME/KEY: MOD_RES
<222> LOCATION: (5)..(5)
<223> OTHER INFORMATION: May be a locked nucleic acid phosphorothioate
      cytidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate cytidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate adenosine
<220> FEATURE:
<221> NAME/KEY: MOD_RES
<222> LOCATION: (10)..(10)
<223> OTHER INFORMATION: May be a locked nucleic acid phosphorothioate
      adenosine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
```

```
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate cytidine
<220> FEATURE:
<221> NAME/KEY: MOD_RES
<222> LOCATION: (15)..(15)
<223> OTHER INFORMATION: May be a locked nucleic acid phosphorothioate
      adenosine
<220> FEATURE:
<221> NAME/KEY: MOD_RES
<222> LOCATION: (16)..(16)
<223> OTHER INFORMATION: May be a phosphorothioate guanosine

<400> SEQUENCE: 106
ctgactccaa gtccag                                                   16

<210> SEQ ID NO 107
<211> LENGTH: 16
<212> TYPE: DNA
<213> ORGANISM: Artificial Sequence
<220> FEATURE:
<223> OTHER INFORMATION: Modified antimiR-378 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      guanosine
<220> FEATURE:
<221> NAME/KEY: MOD_RES
<222> LOCATION: (4)..(4)
<223> OTHER INFORMATION: May be a locked nucleic acid phosphorothioate
      adenosine
<220> FEATURE:
<221> NAME/KEY: MOD_RES
<222> LOCATION: (5)..(5)
<223> OTHER INFORMATION: May be a phosphorothioate cytidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate adenosine
<220> FEATURE:
<221> NAME/KEY: MOD_RES
<222> LOCATION: (10)..(10)
<223> OTHER INFORMATION: May be a locked nucleic acid phosphorothioate
      adenosine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
```

<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(14)
<223> OTHER INFORMATION: May be a locked nucleic acid phosphorothioate
      cytidine
<220> FEATURE:
<221> NAME/KEY: MOD_RES
<222> LOCATION: (15)..(15)
<223> OTHER INFORMATION: May be a phosphorothioate adenosine
<220> FEATURE:
<221> NAME/KEY: MOD_RES
<222> LOCATION: (16)..(16)
<223> OTHER INFORMATION: May be a locked nucleic acid phosphorothioate
      guanosine

<400> SEQUENCE: 107
ctgactccaa gtccag                                                     16

<210> SEQ ID NO 108
<211> LENGTH: 16
<212> TYPE: DNA
<213> ORGANISM: Artificial Sequence
<220> FEATURE:
<223> OTHER INFORMATION: Modified antimiR-29 oligonucleotide
<220> FEATURE:
<221> NAME/KEY: MOD_RES
<222> LOCATION: (1)..(1)
<223> OTHER INFORMATION: May be a locked nucleic acid phosphorothioate
      guanosine
<220> FEATURE:
<221> NAME/KEY: MOD_RES
<222> LOCATION: (2)..(2)
<223> OTHER INFORMATION: May be a phosphorothioate adenosine
<220> FEATURE:
<221> NAME/KEY: MOD_RES
<222> LOCATION: (3)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      cytidine
<220> FEATURE:
<221> NAME/KEY: MOD_RES
<222> LOCATION: (7)..(7)
<223> OTHER INFORMATION: May be a phosphorothioate adenosine
<220> FEATURE:
<221> NAME/KEY: MOD_RES
<222> LOCATION: (8)..(8)
<223> OTHER INFORMATION: May be a locked nucleic acid phosphorothioate
      adenosine
<220> FEATURE:
<221> NAME/KEY: MOD_RES
<222> LOCATION: (9)..(9)
<223> OTHER INFORMATION: May be a phosphorothioate adenosine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a locked nucleic acid phosphorothioate
      guanosine

```
<220> FEATURE:
<221> NAME/KEY: MOD_RES
<222> LOCATION: (12)..(12)
<223> OTHER INFORMATION: May be a phosphorothioate guanosine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a phosphorothioate guanosine
<220> FEATURE:
<221> NAME/KEY: MOD_RES
<222> LOCATION: (15)..(15)
<223> OTHER INFORMATION: May be a locked nucleic acid phosphorothioate
      cytidine
<220> FEATURE:
<221> NAME/KEY: MOD_RES
<222> LOCATION: (16)..(16)
<223> OTHER INFORMATION: May be a locked nucleic acid phosphorothioate
      thymidine

<400> SEQUENCE: 108
gatttcaaat ggtgct                                                   16

<210> SEQ ID NO 109
<211> LENGTH: 16
<212> TYPE: DNA
<213> ORGANISM: Artificial Sequence
<220> FEATURE:
<223> OTHER INFORMATION: Modified antimiR-29 oligonucleotide
<220> FEATURE:
<221> NAME/KEY: MOD_RES
<222> LOCATION: (1)..(1)
<223> OTHER INFORMATION: May be a locked nucleic acid phosphorothioate
      guanosine
<220> FEATURE:
<221> NAME/KEY: MOD_RES
<222> LOCATION: (2)..(2)
<223> OTHER INFORMATION: May be a phosphorothioate adenosine
<220> FEATURE:
<221> NAME/KEY: MOD_RES
<222> LOCATION: (3)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      cytidine
<220> FEATURE:
<221> NAME/KEY: MOD_RES
<222> LOCATION: (7)..(7)
<223> OTHER INFORMATION: May be a phosphorothioate adenosine
<220> FEATURE:
<221> NAME/KEY: MOD_RES
<222> LOCATION: (8)..(8)
<223> OTHER INFORMATION: May be a locked nucleic acid phosphorothioate
      adenosine
<220> FEATURE:
<221> NAME/KEY: MOD_RES
<222> LOCATION: (9)..(9)
<223> OTHER INFORMATION: May be a phosphorothioate adenosine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(12)
<223> OTHER INFORMATION: May be a phosphorothioate guanosine
<220> FEATURE:
<221> NAME/KEY: MOD_RES
<222> LOCATION: (13)..(13)
```

```
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a phosphorothioate guanosine
<220> FEATURE:
<221> NAME/KEY: MOD_RES
<222> LOCATION: (15)..(15)
<223> OTHER INFORMATION: May be a phosphorothioate cytidine
<220> FEATURE:
<221> NAME/KEY: MOD_RES
<222> LOCATION: (16)..(16)
<223> OTHER INFORMATION: May be a locked nucleic acid phosphorothioate
      thymidine

<400> SEQUENCE: 109
gatttcaaat ggtgct                                                    16

<210> SEQ ID NO 110
<211> LENGTH: 16
<212> TYPE: DNA
<213> ORGANISM: Artificial Sequence
<220> FEATURE:
<223> OTHER INFORMATION: Modified antimiR-29 oligonucleotide
<220> FEATURE:
<221> NAME/KEY: MOD_RES
<222> LOCATION: (1)..(1)
<223> OTHER INFORMATION: May be a locked nucleic acid phosphorothioate
      guanosine
<220> FEATURE:
<221> NAME/KEY: MOD_RES
<222> LOCATION: (2)..(2)
<223> OTHER INFORMATION: May be a phosphorothioate adenosine
<220> FEATURE:
<221> NAME/KEY: MOD_RES
<222> LOCATION: (3)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate thymidine
<220> FEATURE:
<221> NAME/KEY: MOD_RES
<222> LOCATION: (6)..(6)
<223> OTHER INFORMATION: May be a locked nucleic acid phosphorothioate
      cytidine
<220> FEATURE:
<221> NAME/KEY: MOD_RES
<222> LOCATION: (7)..(7)
<223> OTHER INFORMATION: May be a phosphorothioate adenosine
<220> FEATURE:
<221> NAME/KEY: MOD_RES
<222> LOCATION: (8)..(9)
<223> OTHER INFORMATION: May be a locked nucleic acid phosphorothioate
      adenosine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(12)
<223> OTHER INFORMATION: May be a phosphorothioate guanosine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a phosphorothioate guanosine
<220> FEATURE:
<221> NAME/KEY: MOD_RES
```

<222> LOCATION: (15)..(15)
<223> OTHER INFORMATION: May be a locked nucleic acid phosphorothioate cytidine
<220> FEATURE:
<221> NAME/KEY: MOD_RES
<222> LOCATION: (16)..(16)
<223> OTHER INFORMATION: May be a phosphorothioate thymidine

<400> SEQUENCE: 110
gatttcaaat ggtgct                                              16

<210> SEQ ID NO 111
<211> LENGTH: 16
<212> TYPE: DNA
<213> ORGANISM: Artificial Sequence
<220> FEATURE:
<223> OTHER INFORMATION: Modified antimiR-29 oligonucleotide
<220> FEATURE:
<221> NAME/KEY: MOD_RES
<222> LOCATION: (1)..(1)
<223> OTHER INFORMATION: May be a locked nucleic acid phosphorothioate guanosine
<220> FEATURE:
<221> NAME/KEY: MOD_RES
<222> LOCATION: (2)..(2)
<223> OTHER INFORMATION: May be a phosphorothioate adenosine
<220> FEATURE:
<221> NAME/KEY: MOD_RES
<222> LOCATION: (3)..(3)
<223> OTHER INFORMATION: May be a locked nucleic acid phosphorothioate thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate thymidine
<220> FEATURE:
<221> NAME/KEY: MOD_RES
<222> LOCATION: (6)..(6)
<223> OTHER INFORMATION: May be a phosphorothioate cytidine
<220> FEATURE:
<221> NAME/KEY: MOD_RES
<222> LOCATION: (7)..(7)
<223> OTHER INFORMATION: May be a locked nucleic acid phosphorothioate adenosine
<220> FEATURE:
<221> NAME/KEY: MOD_RES
<222> LOCATION: (8)..(8)
<223> OTHER INFORMATION: May be a phosphorothioate adenosine
<220> FEATURE:
<221> NAME/KEY: MOD_RES
<222> LOCATION: (9)..(9)
<223> OTHER INFORMATION: May be a locked nucleic acid phosphorothioate adenosine
<220> FEATURE:
<221> NAME/KEY: MOD_RES
<222> LOCATION: (10)..(10)
<223> OTHER INFORMATION: May be a phosphorothioate thymidine
<220> FEATURE:
<221> NAME/KEY: MOD_RES
<222> LOCATION: (11)..(11)
<223> OTHER INFORMATION: May be a locked nucleic acid phosphorothioate guanosine
<220> FEATURE:
<221> NAME/KEY: MOD_RES
<222> LOCATION: (12)..(12)
<223> OTHER INFORMATION: May be a phosphorothioate guanosine
<220> FEATURE:
<221> NAME/KEY: MOD_RES
<222> LOCATION: (13)..(13)
<223> OTHER INFORMATION: May be a locked nucleic acid phosphorothioate thymidine
<220> FEATURE:

<221> NAME/KEY: MOD_RES
<222> LOCATION: (14)..(14)
<223> OTHER INFORMATION: May be a phosphorothioate guanosine
<220> FEATURE:
<221> NAME/KEY: MOD_RES
<222> LOCATION: (15)..(15)
<223> OTHER INFORMATION: May be a locked nucleic acid phosphorothioate
      cytidine
<220> FEATURE:
<221> NAME/KEY: MOD_RES
<222> LOCATION: (16)..(16)
<223> OTHER INFORMATION: May be a locked nucleic acid phosphorothioate
      thymidine

<400> SEQUENCE: 111
gatttcaaat ggtgct                                                      16

<210> SEQ ID NO 112
<211> LENGTH: 16
<212> TYPE: DNA
<213> ORGANISM: Artificial Sequence
<220> FEATURE:
<223> OTHER INFORMATION: Modified antimiR-29 oligonucleotide
<220> FEATURE:
<221> NAME/KEY: MOD_RES
<222> LOCATION: (1)..(1)
<223> OTHER INFORMATION: May be a locked nucleic acid phosphorothioate
      guanosine
<220> FEATURE:
<221> NAME/KEY: MOD_RES
<222> LOCATION: (2)..(2)
<223> OTHER INFORMATION: May be a phosphorothioate adenosine
<220> FEATURE:
<221> NAME/KEY: MOD_RES
<222> LOCATION: (3)..(3)
<223> OTHER INFORMATION: May be a phosphorothioate thymidine
<220> FEATURE:
<221> NAME/KEY: MOD_RES
<222> LOCATION: (4)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate cytidine
<220> FEATURE:
<221> NAME/KEY: MOD_RES
<222> LOCATION: (7)..(7)
<223> OTHER INFORMATION: May be a locked nucleic acid phosphorothioate
      adenosine
<220> FEATURE:
<221> NAME/KEY: MOD_RES
<222> LOCATION: (8)..(8)
<223> OTHER INFORMATION: May be a phosphorothioate adenosine
<220> FEATURE:
<221> NAME/KEY: MOD_RES
<222> LOCATION: (9)..(9)
<223> OTHER INFORMATION: May be a locked nucleic acid phosphorothioate
      adenosine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      guanosine
<220> FEATURE:
<221> NAME/KEY: MOD_RES
<222> LOCATION: (13)..(13)
<223> OTHER INFORMATION: May be a phosphorothioate thymidine
<220> FEATURE:
<221> NAME/KEY: MOD_RES
<222> LOCATION: (14)..(14)
<223> OTHER INFORMATION: May be a locked nucleic acid phosphorothioate
      guanosine
<220> FEATURE:
<221> NAME/KEY: MOD_RES
<222> LOCATION: (15)..(15)
<223> OTHER INFORMATION: May be a phosphorothioate cytidine
<220> FEATURE:
<221> NAME/KEY: MOD_RES
<222> LOCATION: (16)..(16)
<223> OTHER INFORMATION: May be a locked nucleic acid phosphorothioate
      thymidine

<400> SEQUENCE: 112
gatttcaaat ggtgct                                                   16

<210> SEQ ID NO 113
<211> LENGTH: 16
<212> TYPE: DNA
<213> ORGANISM: Artificial Sequence
<220> FEATURE:
<223> OTHER INFORMATION: Modified antimiR-29 oligonucleotide
<220> FEATURE:
<221> NAME/KEY: MOD_RES
<222> LOCATION: (1)..(1)
<223> OTHER INFORMATION: May be a locked nucleic acid phosphorothioate
      guanosine
<220> FEATURE:
<221> NAME/KEY: MOD_RES
<222> LOCATION: (2)..(2)
<223> OTHER INFORMATION: May be a phosphorothioate adenosine
<220> FEATURE:
<221> NAME/KEY: MOD_RES
<222> LOCATION: (3)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      cytidine
<220> FEATURE:
<221> NAME/KEY: MOD_RES
<222> LOCATION: (7)..(7)
<223> OTHER INFORMATION: May be a phosphorothioate adenosine
<220> FEATURE:
<221> NAME/KEY: MOD_RES
<222> LOCATION: (8)..(8)
<223> OTHER INFORMATION: May be a locked nucleic acid phosphorothioate
      adenosine
<220> FEATURE:
<221> NAME/KEY: MOD_RES
<222> LOCATION: (9)..(9)
<223> OTHER INFORMATION: May be a phosphorothioate adenosine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(12)
<223> OTHER INFORMATION: May be a phosphorothioate guanosine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a phosphorothioate guanosine
<220> FEATURE:
<221> NAME/KEY: MOD_RES
<222> LOCATION: (15)..(15)

```
<223> OTHER INFORMATION: May be a locked nucleic acid phosphorothioate
      cytidine
<220> FEATURE:
<221> NAME/KEY: MOD_RES
<222> LOCATION: (16)..(16)
<223> OTHER INFORMATION: May be a phosphorothioate thymidine

<400> SEQUENCE: 113
gatttcaaat ggtgct                                                       16

<210> SEQ ID NO 114
<211> LENGTH: 16
<212> TYPE: DNA
<213> ORGANISM: Artificial Sequence
<220> FEATURE:
<223> OTHER INFORMATION: Modified antimiR-29 oligonucleotide
<220> FEATURE:
<221> NAME/KEY: MOD_RES
<222> LOCATION: (1)..(1)
<223> OTHER INFORMATION: May be a locked nucleic acid phosphorothioate
      guanosine
<220> FEATURE:
<221> NAME/KEY: MOD_RES
<222> LOCATION: (2)..(2)
<223> OTHER INFORMATION: May be a phosphorothioate adenosine
<220> FEATURE:
<221> NAME/KEY: MOD_RES
<222> LOCATION: (3)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate thymidine
<220> FEATURE:
<221> NAME/KEY: MOD_RES
<222> LOCATION: (6)..(6)
<223> OTHER INFORMATION: May be a phosphorothioate cytidine
<220> FEATURE:
<221> NAME/KEY: MOD_RES
<222> LOCATION: (7)..(8)
<223> OTHER INFORMATION: May be a locked nucleic acid phosphorothioate
      adenosine
<220> FEATURE:
<221> NAME/KEY: MOD_RES
<222> LOCATION: (9)..(9)
<223> OTHER INFORMATION: May be a phosphorothioate adenosine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      guanosine
<220> FEATURE:
<221> NAME/KEY: MOD_RES
<222> LOCATION: (13)..(13)
<223> OTHER INFORMATION: May be a phosphorothioate thymidine
<220> FEATURE:
<221> NAME/KEY: MOD_RES
<222> LOCATION: (14)..(14)
<223> OTHER INFORMATION: May be a locked nucleic acid phosphorothioate
      guanosine
<220> FEATURE:
<221> NAME/KEY: MOD_RES
<222> LOCATION: (15)..(15)
<223> OTHER INFORMATION: May be a phosphorothioate cytidine
<220> FEATURE:
<221> NAME/KEY: MOD_RES
<222> LOCATION: (16)..(16)
```

-continued

<223> OTHER INFORMATION: May be a locked nucleic acid phosphorothioate
      thymidine

<400> SEQUENCE: 114
gatttcaaat ggtgct                                                       16

<210> SEQ ID NO 115
<211> LENGTH: 16
<212> TYPE: DNA
<213> ORGANISM: Artificial Sequence
<220> FEATURE:
<223> OTHER INFORMATION: Modified antimiR-199a oligonucleotide
<220> FEATURE:
<221> NAME/KEY: MOD_RES
<222> LOCATION: (1)..(1)
<223> OTHER INFORMATION: May be a locked nucleic acid phosphorothioate
      guanosine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a phosphorothioate adenosine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      cytidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      guanosine
<220> FEATURE:
<221> NAME/KEY: MOD_RES
<222> LOCATION: (9)..(9)
<223> OTHER INFORMATION: May be a phosphorothioate adenosine
<220> FEATURE:
<221> NAME/KEY: MOD_RES
<222> LOCATION: (10)..(10)
<223> OTHER INFORMATION: May be a locked nucleic acid phosphorothioate
      adenosine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a phosphorothioate adenosine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES

```
<222> LOCATION: (15)..(16)
<223> OTHER INFORMATION: May be a locked nucleic acid phosphorothioate
      guanosine

<400> SEQUENCE: 115
gtagtctgaa cactgg                                                    16

<210> SEQ ID NO 116
<211> LENGTH: 16
<212> TYPE: DNA
<213> ORGANISM: Artificial Sequence
<220> FEATURE:
<223> OTHER INFORMATION: Modified antimiR-199a oligonucleotide
<220> FEATURE:
<221> NAME/KEY: MOD_RES
<222> LOCATION: (1)..(1)
<223> OTHER INFORMATION: May be a locked nucleic acid phosphorothioate
      guanosine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a phosphorothioate adenosine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      cytidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a phosphorothioate guanosine
<220> FEATURE:
<221> NAME/KEY: MOD_RES
<222> LOCATION: (9)..(10)
<223> OTHER INFORMATION: May be a locked nucleic acid phosphorothioate
      adenosine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a phosphorothioate adenosine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(16)
<223> OTHER INFORMATION: May be a locked nucleic acid phosphorothioate
      guanosine
```

<400> SEQUENCE: 116
gtagtctgaa cactgg					16

<210> SEQ ID NO 117
<211> LENGTH: 16
<212> TYPE: DNA
<213> ORGANISM: Artificial Sequence
<220> FEATURE:
<223> OTHER INFORMATION: Modified antimiR-199a oligonucleotide
<220> FEATURE:
<221> NAME/KEY: MOD_RES
<222> LOCATION: (1)..(1)
<223> OTHER INFORMATION: May be a locked nucleic acid phosphorothioate
      guanosine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a phosphorothioate adenosine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a phosphorothioate thymidine
<220> FEATURE:
<221> NAME/KEY: MOD_RES
<222> LOCATION: (6)..(6)
<223> OTHER INFORMATION: May be a locked nucleic acid phosphorothioate
      cytidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      guanosine
<220> FEATURE:
<221> NAME/KEY: MOD_RES
<222> LOCATION: (9)..(9)
<223> OTHER INFORMATION: May be a phosphorothioate adenosine
<220> FEATURE:
<221> NAME/KEY: MOD_RES
<222> LOCATION: (10)..(10)
<223> OTHER INFORMATION: May be a locked nucleic acid phosphorothioate
      adenosine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a phosphorothioate adenosine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(16)
<223> OTHER INFORMATION: May be a locked nucleic acid phosphorothioate
      guanosine

<400> SEQUENCE: 117
gtagtctgaa cactgg                                                16

<210> SEQ ID NO 118
<211> LENGTH: 16
<212> TYPE: DNA
<213> ORGANISM: Artificial Sequence
<220> FEATURE:
<223> OTHER INFORMATION: Modified antimiR-199a oligonucleotide
<220> FEATURE:
<221> NAME/KEY: MOD_RES
<222> LOCATION: (1)..(1)
<223> OTHER INFORMATION: May be a locked nucleic acid phosphorothioate
      guanosine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a phosphorothioate adenosine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      cytidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      guanosine
<220> FEATURE:
<221> NAME/KEY: MOD_RES
<222> LOCATION: (9)..(9)
<223> OTHER INFORMATION: May be a phosphorothioate adenosine
<220> FEATURE:
<221> NAME/KEY: MOD_RES
<222> LOCATION: (10)..(10)
<223> OTHER INFORMATION: May be a locked nucleic acid phosphorothioate
      adenosine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a phosphorothioate adenosine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)

```
<223> OTHER INFORMATION: May be a phosphorothioate guanosine
<220> FEATURE:
<221> NAME/KEY: MOD_RES
<222> LOCATION: (16)..(16)
<223> OTHER INFORMATION: May be a locked nucleic acid phosphorothioate
      guanosine

<400> SEQUENCE: 118
gtagtctgaa cactgg                                                        16

<210> SEQ ID NO 119
<211> LENGTH: 16
<212> TYPE: DNA
<213> ORGANISM: Artificial Sequence
<220> FEATURE:
<223> OTHER INFORMATION: Modified antimiR-199a oligonucleotide
<220> FEATURE:
<221> NAME/KEY: MOD_RES
<222> LOCATION: (1)..(1)
<223> OTHER INFORMATION: May be a locked nucleic acid phosphorothioate
      guanosine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a phosphorothioate adenosine
<220> FEATURE:
<221> NAME/KEY: MOD_RES
<222> LOCATION: (4)..(4)
<223> OTHER INFORMATION: May be a locked nucleic acid phosphorothioate
      guanosine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate cytidine
<220> FEATURE:
<221> NAME/KEY: MOD_RES
<222> LOCATION: (7)..(7)
<223> OTHER INFORMATION: May be a locked nucleic acid phosphorothioate
      thymidine
<220> FEATURE:
<221> NAME/KEY: MOD_RES
<222> LOCATION: (8)..(8)
<223> OTHER INFORMATION: May be a phosphorothioate guanosine
<220> FEATURE:
<221> NAME/KEY: MOD_RES
<222> LOCATION: (9)..(10)
<223> OTHER INFORMATION: May be a locked nucleic acid phosphorothioate
      adenosine
<220> FEATURE:
<221> NAME/KEY: MOD_RES
<222> LOCATION: (11)..(11)
<223> OTHER INFORMATION: May be a phosphorothioate cytidine
<220> FEATURE:
<221> NAME/KEY: MOD_RES
<222> LOCATION: (12)..(12)
<223> OTHER INFORMATION: May be a locked nucleic acid phosphorothioate
      adenosine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
```

```
<222> LOCATION: (15)..(15)
<223> OTHER INFORMATION: May be a phosphorothioate guanosine
<220> FEATURE:
<221> NAME/KEY: MOD_RES
<222> LOCATION: (16)..(16)
<223> OTHER INFORMATION: May be a locked nucleic acid phosphorothioate
      guanosine

<400> SEQUENCE: 119
gtagtctgaa cactgg                                                        16

<210> SEQ ID NO 120
<211> LENGTH: 16
<212> TYPE: DNA
<213> ORGANISM: Artificial Sequence
<220> FEATURE:
<223> OTHER INFORMATION: Modified antimiR-92a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(3)
<223> OTHER INFORMATION: May be a locked nucleic acid phosphorothioate
      guanosine
<220> FEATURE:
<221> NAME/KEY: MOD_RES
<222> LOCATION: (4)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a locked nucleic acid phosphorothioate
      adenosine
<220> FEATURE:
<221> NAME/KEY: MOD_RES
<222> LOCATION: (7)..(7)
<223> OTHER INFORMATION: May be a phosphorothioate cytidine
<220> FEATURE:
<221> NAME/KEY: MOD_RES
<222> LOCATION: (8)..(8)
<223> OTHER INFORMATION: May be a locked nucleic acid phosphorothioate
      adenosine
<220> FEATURE:
<221> NAME/KEY: MOD_RES
<222> LOCATION: (9)..(9)
<223> OTHER INFORMATION: May be a phosphorothioate adenosine
<220> FEATURE:
<221> NAME/KEY: MOD_RES
<222> LOCATION: (10)..(10)
<223> OTHER INFORMATION: May be a locked nucleic acid phosphorothioate
      guanosine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a phosphorothioate guanosine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a locked nucleic acid phosphorothioate
      adenosine
```

```
<220> FEATURE:
<221> NAME/KEY: MOD_RES
<222> LOCATION: (15)..(15)
<223> OTHER INFORMATION: May be a phosphorothioate adenosine
<220> FEATURE:
<221> NAME/KEY: MOD_RES
<222> LOCATION: (16)..(16)
<223> OTHER INFORMATION: May be a locked nucleic acid thymidine

<400> SEQUENCE: 120
ccgggacaag tgcaat                                                         16

<210> SEQ ID NO 121
<211> LENGTH: 16
<212> TYPE: DNA
<213> ORGANISM: Artificial Sequence
<220> FEATURE:
<223> OTHER INFORMATION: Modified antimiR-92a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
      guanosine
<220> FEATURE:
<221> NAME/KEY: MOD_RES
<222> LOCATION: (6)..(6)
<223> OTHER INFORMATION: May be a locked nucleic acid phosphorothioate
      adenosine
<220> FEATURE:
<221> NAME/KEY: MOD_RES
<222> LOCATION: (7)..(7)
<223> OTHER INFORMATION: May be a phosphorothioate cytidine
<220> FEATURE:
<221> NAME/KEY: MOD_RES
<222> LOCATION: (8)..(8)
<223> OTHER INFORMATION: May be a locked nucleic acid phosphorothioate
      adenosine
<220> FEATURE:
<221> NAME/KEY: MOD_RES
<222> LOCATION: (9)..(9)
<223> OTHER INFORMATION: May be a phosphorothioate adenosine
<220> FEATURE:
<221> NAME/KEY: MOD_RES
<222> LOCATION: (10)..(10)
<223> OTHER INFORMATION: May be a locked nucleic acid phosphorothioate
      guanosine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a phosphorothioate guanosine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate adenosine
```

```
<220> FEATURE:
<221> NAME/KEY: MOD_RES
<222> LOCATION: (15)..(15)
<223> OTHER INFORMATION: May be a locked nucleic acid phosphorothioate
      adenosine
<220> FEATURE:
<221> NAME/KEY: MOD_RES
<222> LOCATION: (16)..(16)
<223> OTHER INFORMATION: May be a locked nucleic acid thymidine

<400> SEQUENCE: 121
ccgggacaag tgcaat                                                            16

<210> SEQ ID NO 122
<211> LENGTH: 16
<212> TYPE: DNA
<213> ORGANISM: Artificial Sequence
<220> FEATURE:
<223> OTHER INFORMATION: Modified antimiR-92a oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(3)
<223> OTHER INFORMATION: May be a locked nucleic acid phosphorothioate
      guanosine
<220> FEATURE:
<221> NAME/KEY: MOD_RES
<222> LOCATION: (4)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a locked nucleic acid phosphorothioate
      adenosine
<220> FEATURE:
<221> NAME/KEY: MOD_RES
<222> LOCATION: (7)..(7)
<223> OTHER INFORMATION: May be a phosphorothioate cytidine
<220> FEATURE:
<221> NAME/KEY: MOD_RES
<222> LOCATION: (8)..(8)
<223> OTHER INFORMATION: May be a phosphorothioate adenosine
<220> FEATURE:
<221> NAME/KEY: MOD_RES
<222> LOCATION: (9)..(9)
<223> OTHER INFORMATION: May be a locked nucleic acid phosphorothioate
      adenosine
<220> FEATURE:
<221> NAME/KEY: MOD_RES
<222> LOCATION: (10)..(10)
<223> OTHER INFORMATION: May be a locked nucleic acid phosphorothioate
      guanosine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a phosphorothioate guanosine
<220> FEATURE:
<221> NAME/KEY: MOD_RES
<222> LOCATION: (13)..(13)
<223> OTHER INFORMATION: May be a locked nucleic acid phosphorothioate
      cytidine
```

```
<220> FEATURE:
<221> NAME/KEY: MOD_RES
<222> LOCATION: (14)..(14)
<223> OTHER INFORMATION: May be a locked nucleic acid phosphorothioate
      adenosine
<220> FEATURE:
<221> NAME/KEY: MOD_RES
<222> LOCATION: (15)..(15)
<223> OTHER INFORMATION: May be a phosphorothioate adenosine
<220> FEATURE:
<221> NAME/KEY: MOD_RES
<222> LOCATION: (16)..(16)
<223> OTHER INFORMATION: May be a locked nucleic acid thymidine

<400> SEQUENCE: 122
ccgggacaag tgcaat                                                      16
```